(12) United States Patent
Thiery et al.

(10) Patent No.: US 10,509,034 B2
(45) Date of Patent: Dec. 17, 2019

(54) BLADDER CARCINOMA BIOMARKERS

(71) Applicant: Agency for Science, Technology and Research, Singapore (SG)

(72) Inventors: Jean Paul Thiery, Singapore (SG); Prashant Kumar, Singapore (SG); Jayantha Gunaratne, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 138 days.

(21) Appl. No.: 15/034,585

(22) PCT Filed: Nov. 5, 2014

(86) PCT No.: PCT/SG2014/000521
§ 371 (c)(1),
(2) Date: May 5, 2016

(87) PCT Pub. No.: WO2015/069187
PCT Pub. Date: May 14, 2015

(65) Prior Publication Data
US 2016/0274113 A1    Sep. 22, 2016

(30) Foreign Application Priority Data

Nov. 5, 2013 (SG) ................ 201308203-7

(51) Int. Cl.
*C07K 16/00* (2006.01)
*G01N 33/574* (2006.01)
*C12Q 1/6886* (2018.01)

(52) U.S. Cl.
CPC ..... *G01N 33/57407* (2013.01); *C12Q 1/6886* (2013.01); *G01N 33/57484* (2013.01); *C12Q 2600/112* (2013.01); *C12Q 2600/158* (2013.01); *C12Y 301/02* (2013.01); *G01N 2333/47* (2013.01); *G01N 2333/4716* (2013.01); *G01N 2333/775* (2013.01); *G01N 2333/916* (2013.01); *G01N 2560/00* (2013.01)

(58) Field of Classification Search
None
See application file for complete search history.

(56) References Cited

U.S. PATENT DOCUMENTS

| 2009/0208921 A1* | 8/2009 | Tempst ............ G01N 33/57484 435/4 |
| 2009/0209431 A1* | 8/2009 | Villoch ............ G01N 33/57407 506/7 |
| 2011/0195478 A1 | 8/2011 | Chen et al. |
| 2014/0017713 A1 | 1/2014 | Lee et al. |

FOREIGN PATENT DOCUMENTS

| CN | 101300491 A | 11/2008 |
| CN | 102925444 A | 2/2013 |
| CN | 103018461 A | 4/2013 |
| CN | 103235141 A | 8/2013 |
| CN | 103370622 A | 10/2013 |
| JP | 2009-505039 A | 2/2009 |
| JP | 2009-511028 A | 3/2009 |
| JP | 2011-167188 A | 9/2011 |
| JP | 2011-529184 A | 12/2011 |
| WO | WO 2003/003906 A2 | 1/2003 |
| WO | WO 2005/049829 A1 | 6/2005 |
| WO | WO 2007/016716 A1 | 2/2007 |
| WO | WO 2007/042256 A1 | 4/2007 |
| WO | WO 2009/026605 A2 | 3/2009 |
| WO | WO 2010/011357 A2 | 1/2010 |
| WO | WO 2012/115885 A1 | 8/2012 |
| WO | WO 2015/069187 A1 | 5/2015 |

OTHER PUBLICATIONS

Dieplinger et al (Cancer Epidemiol Biomarkers Prev 18: 1127-33, 2009 (Year: 2009).*
Iwaki et al (Cancer Sci 95:955-961, 2004 (Year: 2004).*
Abulaizi et al., The application of a three-step proteome analysis for identification of new biomarkers of pancreatic cancer. Int J Proteomics. 2011;2011:628787. doi: 10.1155/2011/628787.
Boersema et al., Multiplex peptide stable isotope dimethyl labeling for quantitative proteomics. Nat Protoc. 2009;4(4):484-94. doi: 10.1038/nprot.2009.21.
Chen et al., Neural protein gamma-synuclein interacting with androgen receptor promotes human prostate cancer progression. BMC Cancer. Dec. 11, 2012;12:593. doi: 10.1186/1471-2407-12-593.
De Hostos et al., Coronin, an actin binding protein of Dictyostelium discoideum localized to cell surface projections, has sequence similarities to G protein beta subunits. EMBO J. Dec. 1991;10(13):4097-104.
Deng et al., The structure of dimeric apolipoprotein A-IV and its mechanism of self-association. Structure. May 9, 2012;20(5):767-79. doi: 10.1016/j.str.2012.02.020.
Dieplinger et al., Afamin and apolipoprotein A-IV: novel protein markers for ovarian cancer. Cancer Epidemiol Biomarkers Prev. Apr. 2009;18(4):1127-33. doi: 10.1158/1055-9965.EPI-08-0653.
Föger et al., Requirement for coronin 1 in T lymphocyte trafficking and cellular homeostasis. Science. Aug. 11, 2006;313(5788):839-42.
Grossman et al., Detection of bladder cancer using a point-of-care proteomic assay. JAMA. Feb. 16, 2005;293(7):810-6.
Gutiérrez Baños et al., Usefulness of the BTA STAT Test for the diagnosis of bladder cancer. Urology. Apr. 2001;57(4):685-9.
Hwang et al., Use of the NMP22 BladderChek test in the diagnosis and follow-up of urothelial cancer: a cross-sectional study. Urology. Jan. 2011;77(1):154-9. doi: 10.1016/j.urology.2010.04.059.

(Continued)

*Primary Examiner* — Lei Yao
(74) *Attorney, Agent, or Firm* — Wolf, Greenfield & Sacks, P.C.

(57) ABSTRACT

Disclosed are bladder cancer protein biomarkers, methods of determining whether a patient suffers from or shows recurrence of bladder cancer or early stage bladder cancer, or late stage bladder cancer using the bladder cancer protein biomarkers, a detection system, and kits thereof. Said bladder cancer biomarkers comprise at least one of Coronin-IA, Apolipoprotein A-IV, Semenogelin-2, Gamma-synuclein and DJ-1, and variants thereof.

9 Claims, 18 Drawing Sheets

Specification includes a Sequence Listing.

(56) References Cited

OTHER PUBLICATIONS

Jia et al., Stimulation of breast cancer invasion and metastasis by synuclein gamma. Cancer Res. Feb. 1, 1999;59(3):742-7.

Liu et al., Proteomic identification of serum biomarkers for gastric cancer using multi-dimensional liquid chromatography and 2D differential gel electrophoresis. Clin Chim Acta. Jul. 11, 2012;413(13-14):1098-106. doi: 10.1016/j.cca.2012.03.003.

Rouwette et al., Identification of coronin-1a as a novel antibody target for clinically isolated syndrome and multiple sclerosis. J Neurochem. Aug. 2013;126(4):483-92. doi: 10.1111/jnc.12335.

Sanchez-Carbayo et al., Profiling bladder cancer using targeted antibody arrays. Am J Pathol. Jan. 2006;168(1):93-103.

Wilson et al., Gene expression profiling of adult acute myeloid leukemia identifies novel biologic clusters for risk classification and outcome prediction. Blood. Jul. 15, 2006;108(2):685-96.

First Office Action for Chinese Application No. 201480072318.9, dated Mar. 31, 2017.

PCT/SG2014/000521, Jan. 22, 2015, International Search Report and Written Opinion.

PCT/SG2014/000521, Feb. 15, 2016, International Preliminary Report on Patentability.

Singapore Written Opinion for Singapore Application No. 11201603563T dated Feb. 16, 2017.

[No Author Listed], *Homo sapiens* coronin, actin binding protein, 1A (CORO1A), transcript variant 1, mRNA. NCBI Accession No. NM_001193333.1. Available at http://www.ncbi.nlm.nih.gov/nuccore/300934761. Submitted Jul. 23, 2010.

[No Author Listed], *Homo sapiens* semenogelin II (SEMG2), mRNA. NCBI Accession No. NM_003008.1. Available at http://www.ncbi.nlm.nih.gov/nuccore/4506884. Submitted Oct. 6, 2003.

Iwaki et al., Diagnostic potential in bladder cancer of a panel of tumor markers (calreticulin, gamma-synuclein, and catechol-o-methyltransferase) identified by proteomic analysis. Cancer Sci. Dec. 2004;95(12):955-61.

Kumar et al., Highly sensitive and specific novel biomarkers for the diagnosis of transitional bladder carcinoma. Oncotarget. May 30, 2015;6(15):13539-49.

Lee et al., Overexpression of DJ-1 and HSP90α, and loss of PTEN associated with invasive urothelial carcinoma of urinary bladder: Possible prognostic markers. Oncol Lett. Mar. 2012;3(3):507-512. Epub Dec. 13, 2011.

Tsujita et al., Proteome of acidic phospholipid-binding proteins: spatial and temporal regulation of Coronin 1A by phosphoinositides. J Biol Chem. Feb. 26, 2010;285(9):6781-9. doi: 10.1074/jbc.M109.057018. Epub Dec. 22, 2009.

Extended European Search Report for European Application No. 14860176.8 dated May 4, 2017.

Greiner et al., Principles and practical application of the receiver-operating characteristic analysis for diagnostic tests. Prev Vet Med. May 30, 2000;45(1-2):23-41. Review. PubMed PMID: 10802332.

* cited by examiner

Antibody: *Complement factor H*
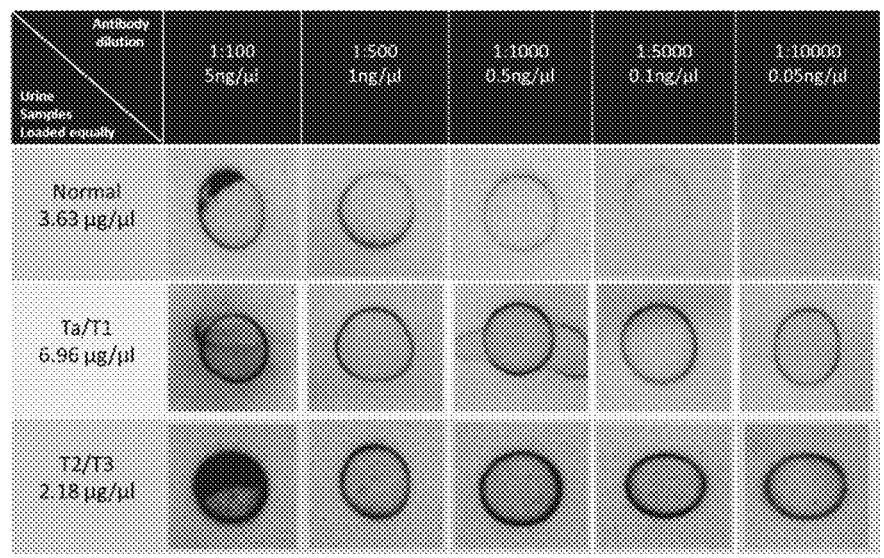
Antibody: *Coronin1A*
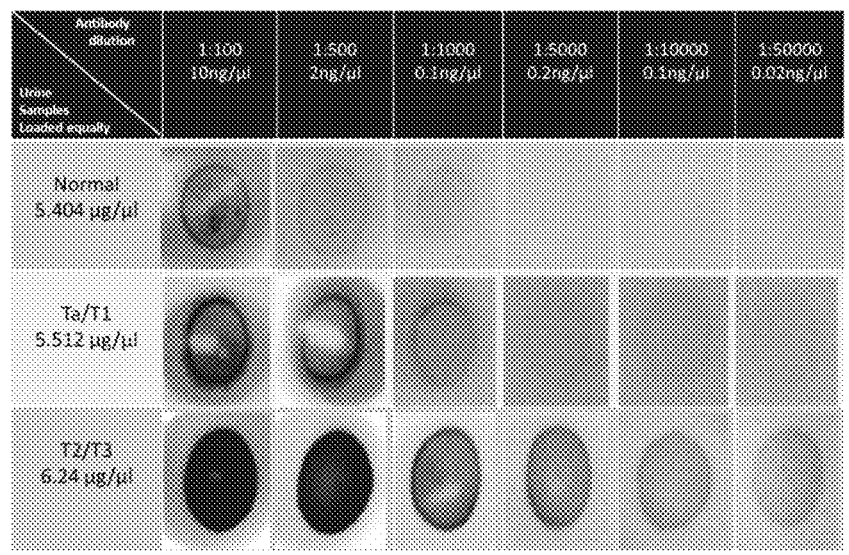
Fig. 3

Antibody: *Apolipoprotein A4*
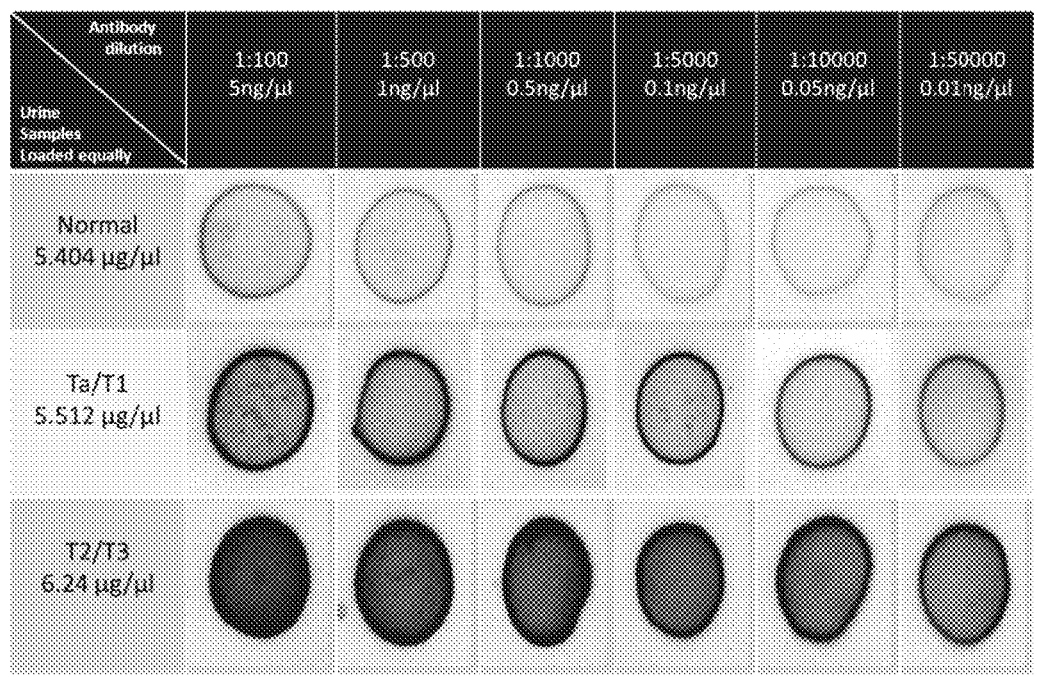
Antibody: *Semenogelin-2*
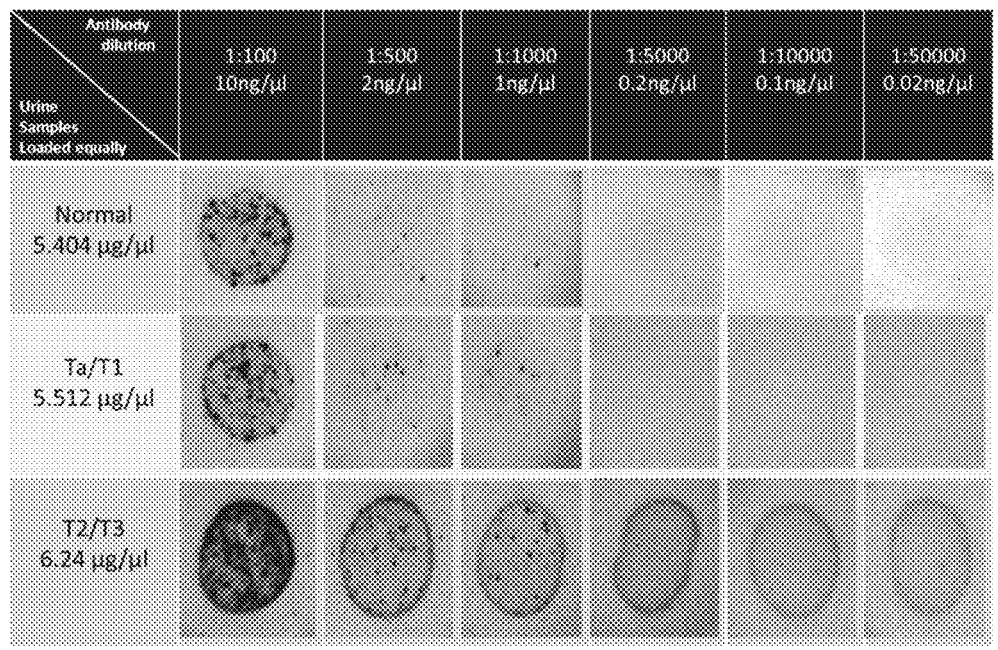
Fig. 3 (continued)

Antibody: *Gamma synuclein*
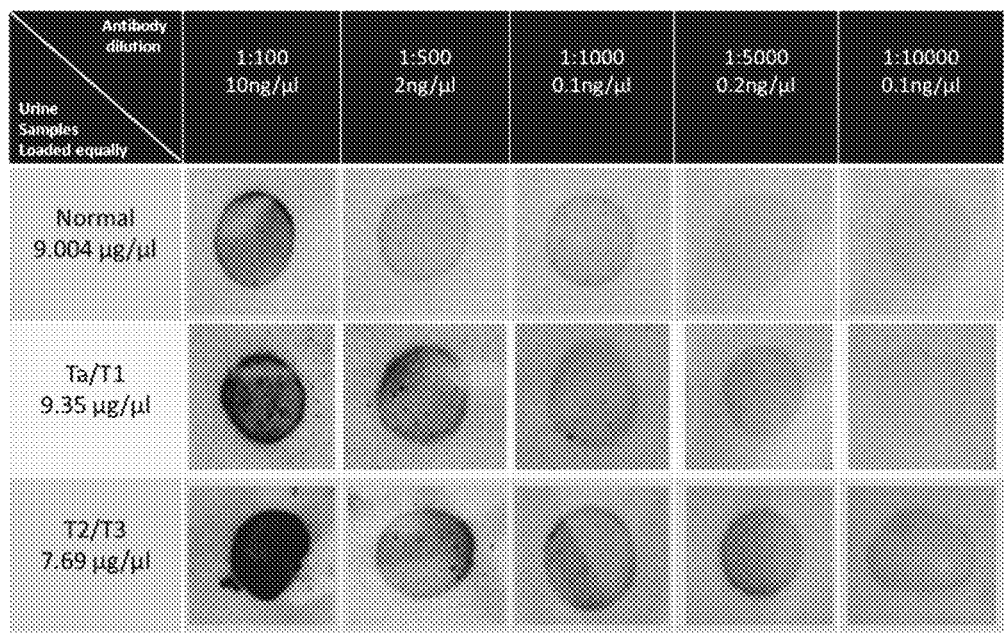
Antibody: *DJ-1*
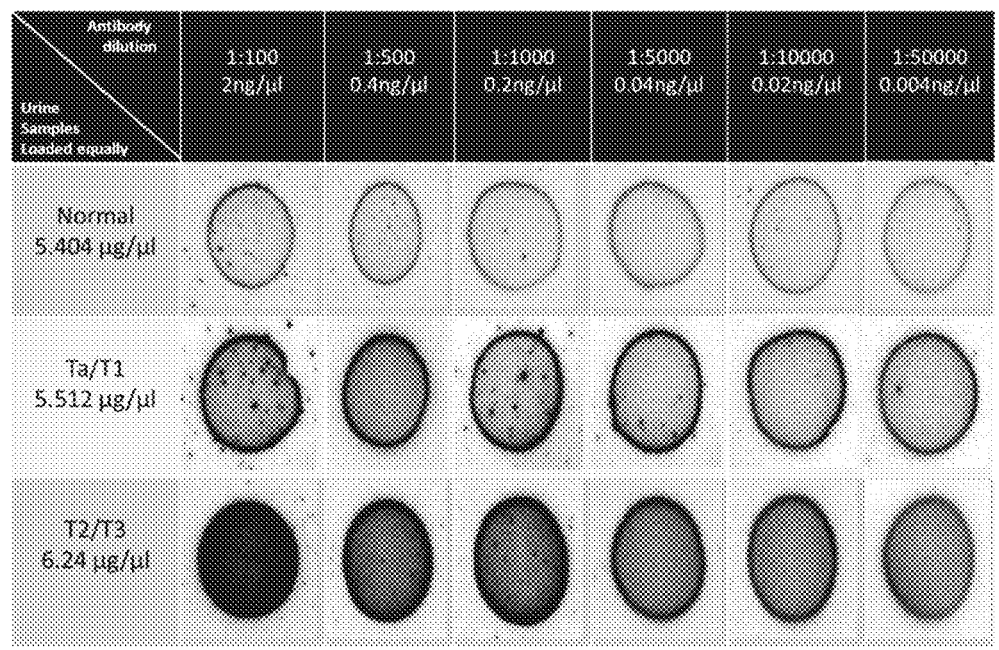
Fig. 3 (continued)

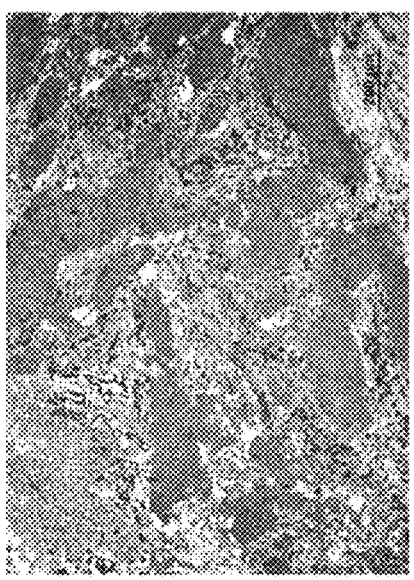
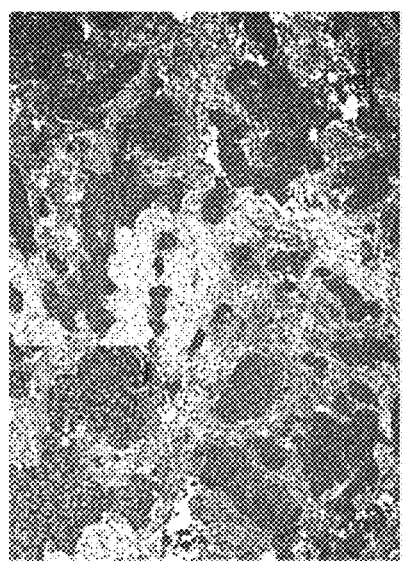
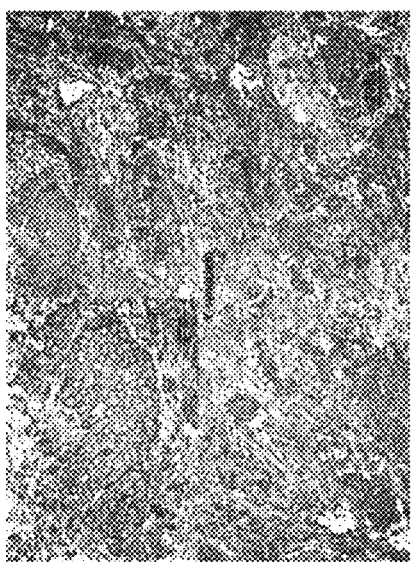
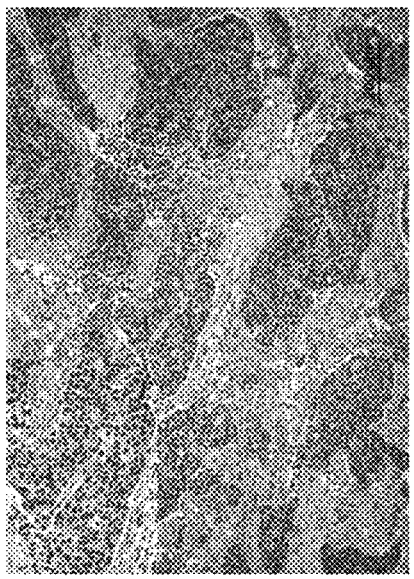
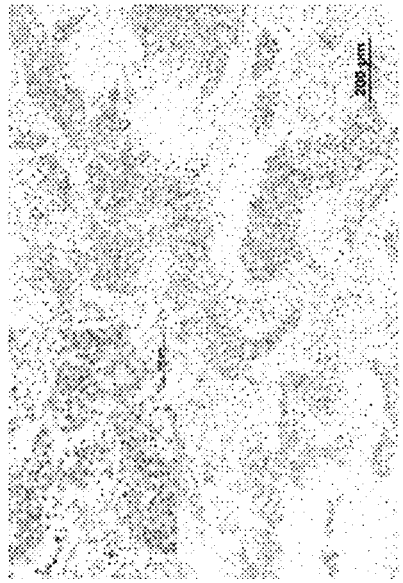
Fig. 14

BLADDER CARCINOMA BIOMARKERS

CROSS-REFERENCE TO RELATED APPLICATIONS

This application is a national stage filing under 35 U.S.C. § 371 of international application number PCT/SG2014/000521, filed Nov. 5, 2014, which claims the benefit of priority of Singapore provisional application No. 201308203-7, filed Nov. 5 2013, the contents of each of which are hereby incorporated by reference in their entirety for all purposes.

FIELD OF THE INVENTION

The present invention relates to biochemistry in particular biomarkers. In particular, the present invention relates to biomarkers associated with bladder carcinoma and methods of using the biomarkers to determine the likelihood that a patient suffers from or shows recurrence of bladder cancer, or early stage bladder cancer, or late stage bladder cancer.

BACKGROUND OF THE INVENTION

Bladder cancer (or bladder carcinoma) is prevalent in developed countries, particularly among men. Bladder cancer is also the fifth most common cancer and results in significant morbidity and mortality. Bladder cancer is notoriously among the most aggressive tumours as soon as they reach stage 2 (T2). Early detection and monitoring of early stage bladder cancer (Ta, T1 stages) patients is critical since these tumours are well-known to recur with high frequency and ultimately progress to T2 stage.

Early detection of bladder cancer requires invasive procedures for confirmed diagnosis. For example, cystoscopy and cytology are still the gold standards for the detection and follow-up of bladder carcinoma. However, these methods cannot detect certain lesions, such as small carcinoma in situ, and are often employed whenever patients present with other clinical signs.

As non-invasive urinary tests are highly desirable for both patient and healthcare system, multiple attempts to develop bladder cancer biomarkers have been made in order to substitute or complement invasive diagnosis such as cystoscopy.

New biomarkers, based on DNA methylation profiling, point mutations and microRNAs, have been established in addition to many proposed protein biomarkers for use in detecting bladder cancer. Commercially available urine-based diagnostic protein markers have also been developed. However, so far, none of the single biomarker assays known in the art adequately address early detection of bladder cancer. For example, tests that measure Nuclear Matrix Protein 22 (NMP22) and Bladder Tumour Antigen (BTA) are currently available commercially and have been approved by the U.S. Food and Drug Administration (FDA) for bladder carcinoma diagnosis. However, these tests rely on single-marker assays that are known to lack specificity.

As none of the single biomarker assays known in the art adequately address early detection of bladder cancer, there is a need to provide an alternative assay that is able to address early detection of bladder cancer. For example, two multiplex protein signatures of ten biomarkers or eight biomarkers have been developed and known in the art. However, none of these currently available diagnostic marker assays have offered sufficient sensitivity and specificity to be routinely used in the clinic.

In view of the above, there is a need to provide an alternative bladder cancer protein biomarker. There is also a need to provide an alternative detection system for non-invasive detection of bladder cancer in a patient. There is also a need to provide an alternative method of determining whether a patient suffers from or shows recurrence of bladder cancer or early stage bladder cancer or late stage bladder cancer.

SUMMARY OF THE INVENTION

In one aspect, there is provided a bladder cancer protein biomarker, wherein the biomarker is at least one selected from the group of consisting of Coronin-1A, Apolipoprotein A-IV, Semenogelin-2, Gamma-synuclein and DJ-1.

In another aspect, there is provided a detection system comprising a) a receiving section to receive a fluid sample from a patient suspected to suffer from bladder cancer and wherein the fluid sample is suspected to comprise one or more biomarkers according to the present disclosure and b) a detection section comprising a substance or substances capable to detect one or more biomarkers according to the present disclosure.

In yet another aspect, there is provided a method of determining whether a patient suffers from or shows recurrence of bladder cancer or early stage bladder cancer or late stage bladder cancer, wherein the method comprises detecting the presence of one or more biomarkers according to the present disclosure.

In yet another aspect there is provided a kit comprising a detection system according to the present disclosure and substances needed to carry out the method according to the present disclosure.

BRIEF DESCRIPTION OF THE DRAWINGS

The invention will be better understood with reference to the detailed description when considered in conjunction with the non-limiting examples and the accompanying drawings, in which:

FIG. 2 shows that the biomarkers of the present disclosure are at least comparative to the commercially available BTA-TRAK assay for complement factor H.

FIG. 3 shows results of rapid-based detection of bladder carcinoma using dot blot assay utilizing the biomarkers of the present disclosure. Urine samples obtained from normal subject, Ta/T1 (non-muscle invasive) and T2/T3 (muscle invasive) bladder carcinoma patient. The dot-blot assay results are: normal subject shows detectable level (negative; low or none); Ta/T1 shows detectable level (+) of the markers; and T2/T3 shows a high level (++) of the target markers. Thus, illustrating the biomarkers of the present disclosure is comparable with Complement factor H in detecting and differentiating normal subject and patients having Ta/T1 (non-muscle invasive) and T2/T3 (muscle invasive) bladder carcinoma.

FIG. 5 clearly shows that the biomarkers of the present disclosure in various combinations perform better in sensitivity and specificity tests as compared to BTA-TRAK test. Thus, demonstrating the biomarkers of the present disclosure provides more sensitive and specific test for bladder carcinoma patients.

FIG. 6 shows the level of all of the five biomarkers of the present disclosure to be significantly higher in Ta/T1 and T2/T3 urine samples compared to healthy subject urine sample or blood plasma. Thus, confirming the biomarkers of the present disclosure is specific for bladder cancer and for detection in urine samples obtained from subjects with bladder carcinoma.

FIG. 7a shows the biomarkers of the present disclosure provides for a highly sensitive and specific biomarkers for both Ta/T1 (non-muscle invasive) bladder carcinoma and T2/T3 (muscle invasive) bladder carcinoma that can be used in ELISA analysis of urine sample.

FIG. 7b shows the biomarkers of the present disclosure provides for a highly sensitive and specific biomarkers for both Ta/T1 (non-muscle invasive) bladder carcinoma and T2/T3 (muscle invasive) bladder carcinoma that can be used in Western Blot analysis of urine samples.

FIG. 8 shows significantly higher fold change in expression in urine samples obtained from patients with Ta/T1 (non-muscle invasive) bladder carcinoma and patients with T2/T3 (muscle invasive) bladder carcinoma as compared to that in healthy subjects. Thus, illustrating the biomarkers of the present disclosure can be used for non-invasive detection of bladder carcinoma in a subject.

FIG. 9 shows at least three out of five biomarkers of the present disclosure are consistently found to be present in bladder carcinoma patients. Thus, demonstrating the biomarkers of the present disclosure can be reliably used for non-invasive detection of bladder carcinoma in a subject.

FIG. 11 shows relative abundance versus mass-to-charge ratio (m/z) of potential markers from the triple-label urine sample analysis. The peptide of respective protein originated from normal urine, Ta/T1 and T2/T3 patients' samples are indicated with arrows and texts that label each peak respectively. The candidate biomarkers were identified by multiplex peptide stable isotope labelling (i.e. reductive dimethyl labelling and mass spectrometry).

FIG. 12 validates the specificity of the biomarker of the present disclosure with 100 μg protein from each voided urine samples obtained from patients suffering from various types of chronic ailments (n=120). FIG. 12 shows that the biomarkers of the present disclosure are consistently absent in samples obtained from non-bladder carcinoma patients. Thus, demonstrating the specificity of the biomarkers of the present disclosure to bladder carcinoma.

FIG. 13 validates the specificity of the biomarker of the present disclosure with 100 μg protein from each voided urine samples obtained from patients suffering from various types of cancers (n=88). FIG. 13 shows that the biomarkers of the present disclosure are consistently absent in samples obtained from non-bladder carcinoma patients suffering from other types of cancers. Thus, demonstrating the specificity of the biomarkers of the present disclosure to bladder carcinoma.

FIG. 14 is an immunohistochemical staining of histological samples obtained from a patient with bladder carcinoma showing the five biomarkers of the present disclosure to be equally enriched in the bladder carcinoma tissue. Thus, showing the five biomarkers of the present disclosure can be used for detecting bladder carcinoma and are specific for bladder cancer.

BRIEF DESCRIPTION OF THE TABLES

Figure 1:
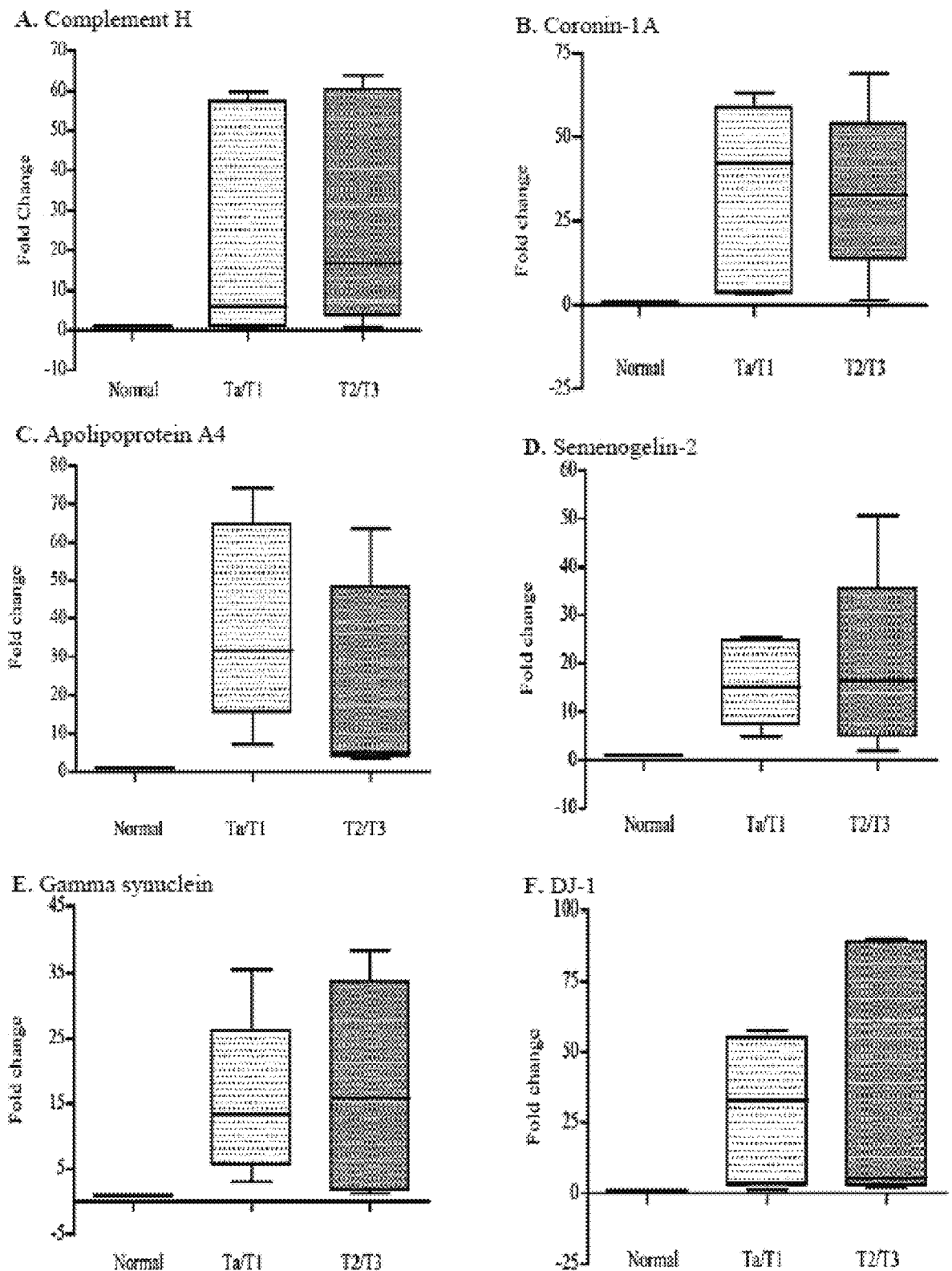
FIG. 1 shows the results of quantitative real-time PCR analysis that verifies (A) Complement H (BTA-TRAK assay), (B) Coronin-1A, (C) Apolipoprotein A, (D) SEmenogelin-2, (E) Gamma synuclein and (F) DJ-1 mRNA expression in Ta/T1 and T2/T3 bladder carcinoma cancer patient samples compared with healthy subjects (i.e. normal individuals). The graphs represent the analysed data of five subjects from each group for a particular marker expression. The mRNA expression of Complement H (BTA-TRAK assay) was also checked for comparison basis. All the values are statistically significant with a p value≤0.05.
Figure 2:
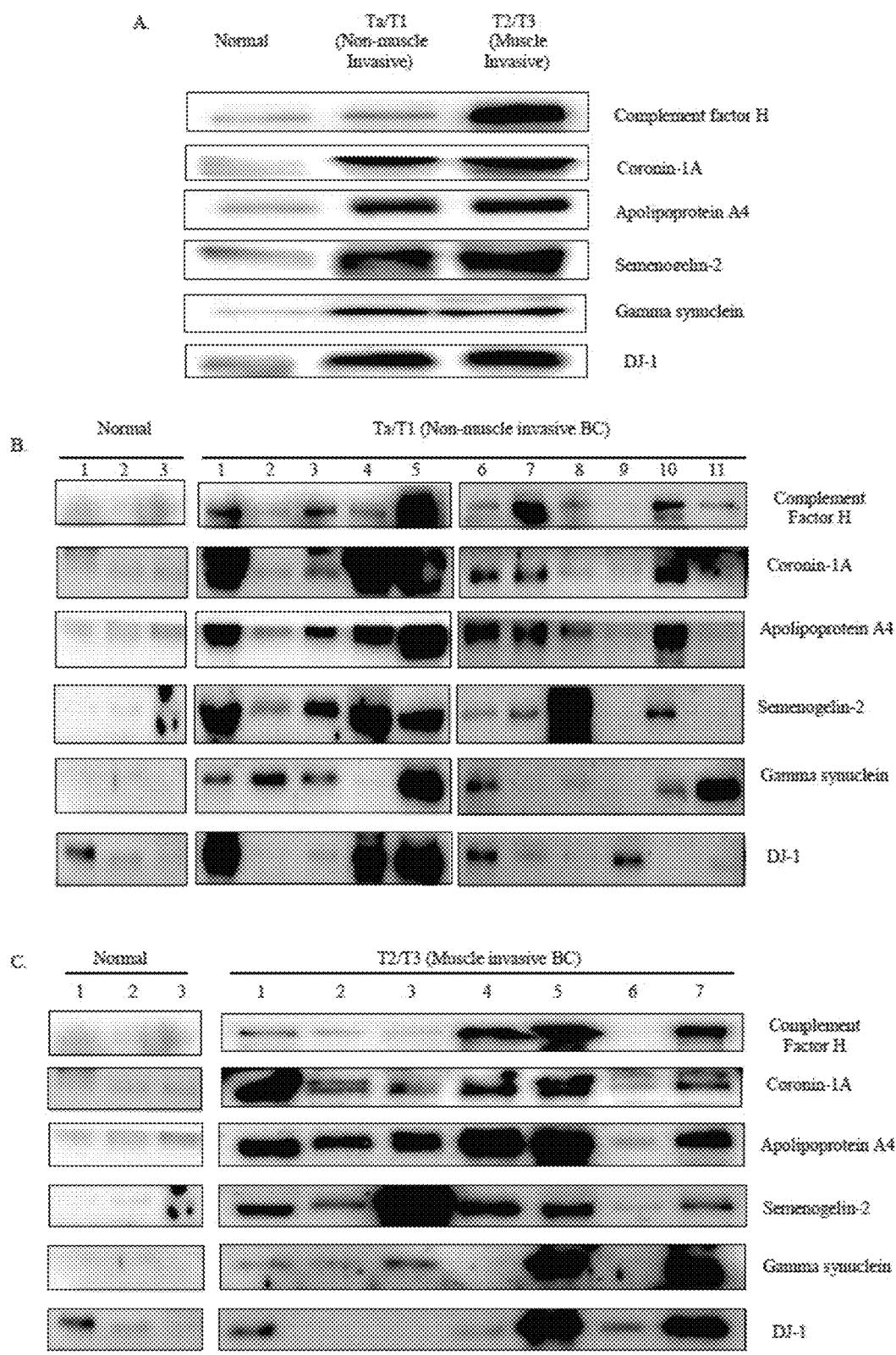
FIG. 2 shows Western Blot analysis comparing the expression of the five biomarkers of the present disclosures in samples obtained from (A) pooled urine samples of normal subjects, Ta/T1 (non-muscle invasive) and T2/T3 (muscle invasive) bladder carcinoma patients; (B) urine samples of three normal subjects and eleven Ta/T1 (non-muscle invasive) bladder carcinoma patients; or (C) urine samples of three normal subjects and seven T2/T3 (muscle invasive) bladder carcinoma patients. The protein expression of the biomarkers were compared with the BTA-TRAK assay for complement factor H.

Table 1 lists the demographic and clinicopathologic characteristics of normal/non cancer subject and cancer subject study cohort of Example 1 of the Experimental Section of the present disclosure.

Table 2A lists antibodies used in the Western Blot and Dot Blot analysis of Example 1 of the Experimental Section of the present disclosure.

Table 2B lists antibodies used in immunohistochemistry analysis of Example 1 of the Experimental Section of the present disclosure.

Table 3 lists the number of urinary markers detected in each patient group of Example 1 of the Experimental Section of the present disclosure.

Table 4 lists results of Western blot analysis of detection using the biomarkers of the present disclosure as compared to Complement H.

Table 5 lists the performance values for individual biomarkers of the present disclosure and three different combinations.

Table 6 lists the clinical information of patients studied in the Example 2 of Experimental Section of the present disclosure.

Table 7 lists the primer sequences for quantitative reverse transcription polymerase chain reaction (q RT-PCR) used in Example 2 of Experimental Section of the present disclosure.

Table 8 lists the antibodies and ELISA kits used for Western Blot, immunostaining and ELISA assays as described in Example 2 of Experimental Section of the present disclosure.

Table 9A lists results of the study of accuracy of combination model in diagnosing Ta/T1 bladder cancer of Example 2 of Experimental Section of the present disclosure.

Table 9B lists results of the study of the accuracy of combination model in diagnosing T2/T3 bladder cancer of Example 2 of Experimental Section of the present disclosure.

Table 10 lists the concentration of the biomarkers of the present disclosure in blood plasma (data obtained from database).

Table 11 lists results of Pearson correlation analysis of biomarker levels in blood plasma and white blood cell of Example 2 of Experimental Section of the present disclosure.

Table 12A lists results on the study of accuracies and thresholds of biomarkers in Ta/T1 diagnosis using both ELISA and Western Blot in urine sample data analysis as presented in Example 2 of Experimental Section of the present disclosure.

Table 12B lists results of the study of the accuracies and thresholds of biomarkers in T2/T3 diagnosis using both ELISA and Western Blot in urine samples data analysis as presented in Example 2 of Experimental Section of the present disclosure.

DETAILED DESCRIPTION OF THE PRESENT INVENTION

Bladder cancer (carcinoma) is amongst the five most common malignancies worldwide. More than 80% of bladder cancer are non-muscle invasive (Ta/T1), which have a 5-year survival rate of >90%. However, approximately 70% of patients with these lesions develop tumour recurrence within two years of initial diagnosis. If left untreated, initially non-invasive tumours (Ta/T1) can progress to muscle-invasive tumours (T2/T3), which have a significantly reduced 5-year survival rate. This clinical observation prompts the development of an accurate diagnostic method for early detection of bladder cancer or bladder cancer recurrences.

Traditionally, cystoscopy and urine cytology are the standard diagnostic tests for bladder carcinoma in a patient. However, cystoscopy is an invasive procedure that causes patient discomfort, requires local or general anaesthesia, relatively expensive and lacks sensitivity as visibility can be reduced due to bleeding. Furthermore, cystoscopy cannot detect certain lesions, such as small carcinoma in situ. Urine cytology also has disadvantages such as detection requires a trained cytopathologist, low sensitivity and costly. Both cystoscopy and urine cytology are also only performed when a patient has other clinical symptoms, which signs the patient could be in a more advance stage. As mentioned above, if left untreated, bladder carcinoma can escalate to a more advance stage that can reduce the patient's survival rate significantly. As such, there is a need to provide for an alternative method for detecting bladder cancer non-invasively.

Much effort has been developed to detect a reliable tumour marker for bladder cancers. Commercially available assay-based and FDA-approved diagnostic methods include bladder tumour antigen (BTA-STAT) and nuclear matrix protein 22 (NMP-22). However, these bioassays are known for their limited sensitivity. Furthermore, these known assays cannot cope with the complexity of bladder carcinoma that typically presents between individuals (subjects).

In view of the above problems, the inventors of the present disclosure have set out to provide alternative biomarker(s) for bladder cancer. Accordingly, there is provided a bladder cancer protein biomarker. As used herein, the term "bladder cancer" or "bladder carcinoma", which terms are used interchangeably, refers to cancer that forms in tissues of the bladder, which is the organ that stores urine. The term "bladder cancer" as used herein may include transitional cell carcinomas (cancer that begins in cells that normally make up the inner lining of the bladder), squamous cell carcinoma (cancer that begins in thin, flat cells) and adenocarcinoma (cancer that begins in cells that make and release mucus and other fluids). In one example, the term refers to urothelial cell carcinoma (also known as "transitional cell carcinoma", "transitional bladder carcinoma" or "transitional bladder cancer") which account for 90 percent of bladder cancers in industrial countries. The symptoms and implications accompanying bladder cancer are well known in the art, like blood in the urine, pain during urination, frequent urination or feeling the need to urinate without being able to do so. In one example, the "bladder cancer" refers to disease in which the cells lining the urinary bladder lose the ability to regulate their growth resulting in a mass of cells that form a tumor. In one example, the term encompasses numerous types of malignant growths of the urinary bladder. It is well known that bladder cancer carries a broad spectrum of aggressiveness and risk. Thus, in one example, bladder cancer or bladder carcinoma as used herein refers to the different stages of bladder carcinoma that can be divided into two major stages of: early stage or non-muscle invasive bladder carcinoma (Ta/T1) and late stage or muscle-invasive bladder carcinoma (T2/T3). Early stage or non-muscle invasive bladder carcinoma includes distinct stages such as: Tis is defined as carcinoma being in situ ("flat tumor"); Ta is when carcinoma is found to be non-invasive papillary; T1 is when carcinoma is found to have invaded subepithelial connective tissue. Late stage or muscle-invasive bladder carcinoma includes three distinct stages where T2 is when carcinoma is found to have invaded muscle; T3 is when carcinoma is found to have invaded perivesical tissue (i.e. near the bladder); and T4 is when carcinoma is found to have invaded adjacent organs like prostate, uterus or vagina followed by pelvic wall or abdominal wall. T2 can be further subdivided into two sub-stages where T2a is when carcinoma is found to have invaded superficial muscle (inner half) and T2b is when carcinoma is found to have invaded deep muscle (outer half). T3 can also be further subdivided into two sub-stages where T3a is when carcinoma is found to have invaded perivesical tissue microscopically and T3b is when carcinoma is found to have invaded perivesical tissue macroscopically (extravesical mass).

As used herein, the term "biomarker" refers to molecular indicators of a specific biological property, a biochemical feature or facet that can be used to determine the presence or absence and/or severity of a particular disease or condition. In the present disclosure, the term "biomarker" refers to a polypeptide, a fragment or variant of such a polypeptide being associated to bladder cancer. Variants of said polypeptide may include polypeptides which differ in their amino acid sequence due to the presence of conservative amino acid substitutions. For example, such variants have an amino acid sequence being at least 70%, at least 80%, at least 90%, at least 95%, at least 98%, or at least 99% identical over the entire sequence region to the amino acid sequences of the specific polypeptides. Variants may be allelic variants, splice variants or any other species specific homologs, paralogs, or orthologs. In one example, the percent identity can be determined by the algorithms known in the art. The sequence identity values recited above in percent (%) are to be determined, preferably, using programs known in the art, for example, Blasts and the like.

The term "protein", "peptide" and "polypeptide", as used herein, are used interchangeably and in their broadest sense refer to a compound of two or more subunit amino acids, amino acid analogs or peptidomimetics. The subunits may be linked by peptide bonds. A protein or peptide must contain at least two amino acids and no limitation is placed on the maximum number of amino acids which may comprise a protein's or peptide's sequence. As used herein the term "amino acid" refers to natural and/or unnatural or synthetic amino acids, including glycine and both the D and L optical isomers, amino acid analogs and peptidomimetics.

In one example, the bladder cancer protein biomarker of the present disclosure may include at least any one of the biomarkers selected from the group consisting of coronin-1A, apolipoprotien A-IV, semenogelin-2, gamma-synuclein and DJ-1. Each of these five proteins has an important biological function, which are further discussed below.

Coronin-1A refers to the protein that is highly expressed in the hematopoietic system and regulates F-actin content in thymocytes. Gene expression studies have shown its altered expression in lymphomas and in other haematological malignancies. Coronin-1A has also been identified as a novel antibody target for clinically isolated syndrome and multiple sclerosis.

Apolipoprotein A-4, also known as apoA-IV, apoAIV, or apoA4, refers to the protein that is synthesized primarily in the intestine and secreted in the plasma. Apolipoprotein A-4 plays a central role in lipid absorption, transport, and metabolism within the reverse cholesterol transport pathway and may act as a postprandial satiety signaling factor and as an antioxidant. This biomarker also shows association with various cancer types, including gastric, pancreatic and ovarian cancers.

The third biomarker, Gamma synuclein, refers to a member of the synuclein family of proteins, which also comprises alpha and beta subtypes. Gamma synuclein has been found in advanced breast, ovarian, gastric, oesophagus, liver, colon, pancreatic, and bladder cancers, and has been shown to promote cancer invasion and metastasis both in vitro and in animal models.

Semenogelin-2, the fourth biomarker, refers to a secreted protein involved in liquefaction of the human semen coagulum and the progressive release of motile spermatozoa A. Semenogelin-2 is detected in small cell lung carcinoma cell lines.

Finally, DJ-1 refers to the protein product of PARK7 (Parkinson disease 7), and it positively regulates androgen receptor-dependent transcription. Overexpression of DJ-1 and correlation with tumour progression has been documented in breast, lung, blood, prostate, cervix, thyroid and pancreas malignancies.

As illustrated in the Experimental Section below, the bladder cancer protein biomarker of the present disclosure may be used individually, or in combination with one another. Thus, in one example, the bladder cancer protein biomarker may comprise any one, two, three, four or all five biomarkers comprising Coronin-1A, Apolipoprotein A-IV, Semenogelin-2, gamma-synuclein and DJ-1. Various examples of combinations of protein biomarkers are exemplified in the Experimental Section below, for example at Tables 9A, 9B and 4. In one example, the biomarkers may comprise Coronin-1A, Apolipoprotein A-IV, Semenogelin-2, gamma-synuclein and DJ-1. In another example, the biomarkers may comprise Coronin-1A, Apolipoprotein A-IV, gamma-synuclein (e.g. FIG. 5 and Table 5). In yet another example, the biomarkers may comprise Coronin-1A, Apolipoprotein A-IV, and DJ-1 (e.g. in Table 9A). In yet another example, the biomarkers may comprise Coronin-1A, Apolipoprotein A-IV, Semenogelin-2, and DJ-1 (e.g. in Table 9A). As illustrated in the Experimental Section, the biomarkers of the present disclosure can be combined with one another and still provide highly sensitive and specific determination of bladder cancer patients. The possibility of combining the biomarkers of the present disclosure is advantageous as it would ensure detection of bladder cancer, which is notorious for having significant genetic heterogeneity and complex somatic mutation between individuals (subjects).

Figure 6:
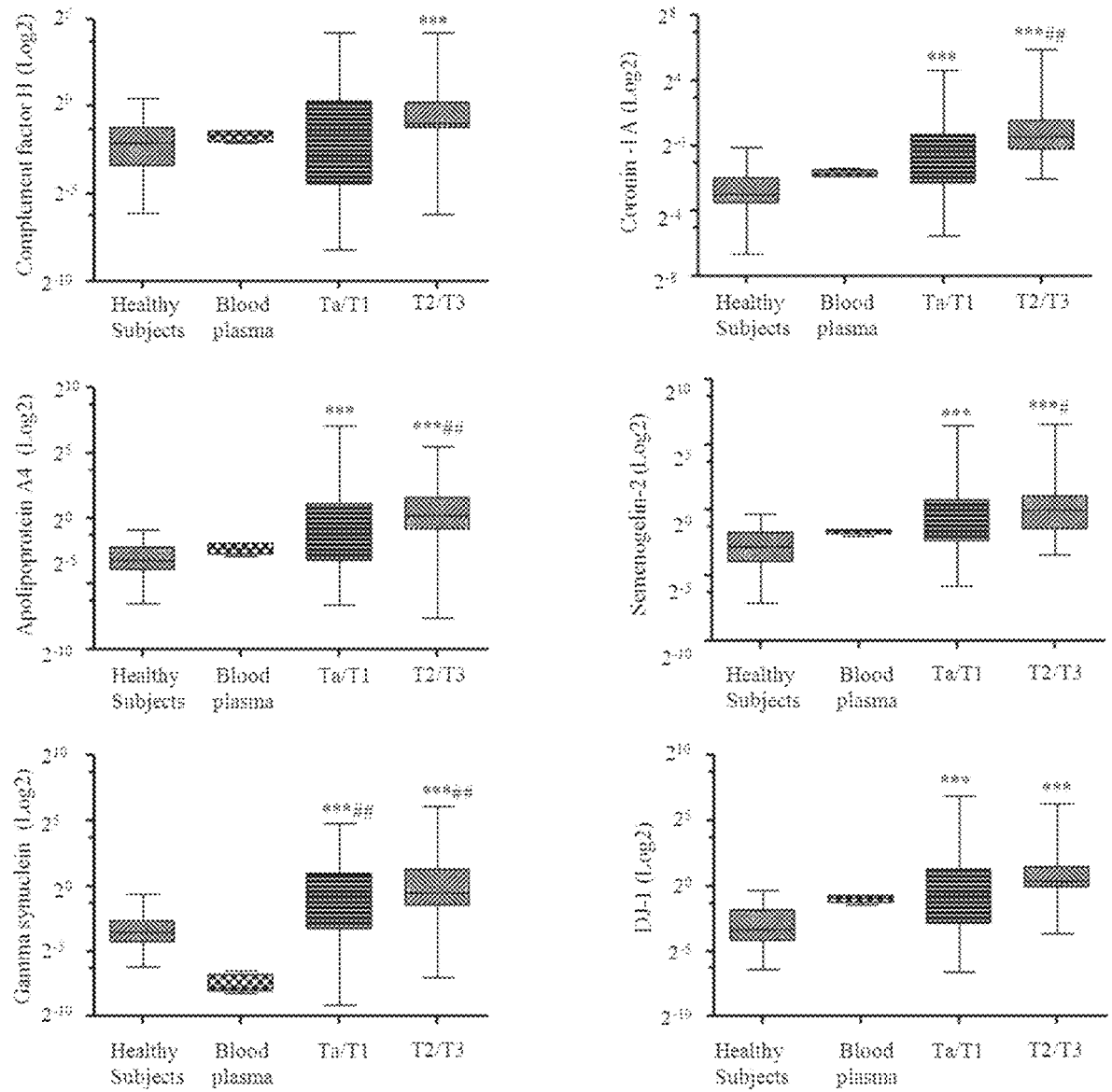
FIG. 6 shows a box and whiskers plot of results of Western Blot analysis of the expression of the five biomarkers of the present disclosure (Coronin-1A, Apolipoprotein A4, Semenogelin-2, Gamma Synuclein, and DJ-1) as compared to control Complement factor H in urine samples of Ta/T1 (non-muscle invasive) bladder carcinoma subjects, T2/T3 (muscle invasive) bladder carcinoma subjects and healthy subjects. The level of biomarkers in blood plasma of healthy subjects is also shown as relative intensity (log 2) to albumin. Results are of healthy subjects (n=30), blood plasma (n=4), Ta/T1 (n=66), and T2/T3 (n=28) urine samples. The box represents the lower quartile, median and higher quartile; The whiskers shows the minimum and maximum values. Mann-Whitney test was used to compute significance. p value for comparison to normal: *$p<0.05$, $p<0.01$, *$p<0.001$. p value for comparison to blood plasma: #$p<0.05$, ##$p<0.01$, ###$p<0.001$. Therefore.

Additionally, the inventors of the present disclosures found that the biomarkers as described herein are indicative of the various stages of bladder cancer. In one example, the biomarkers of the present disclosure may be indicative for early stage (Ta/T1) bladder cancer. For example, Table 9A and Table 12A show that the biomarker(s) of the present disclosure (when used either individually or in combination with one another) provides better sensitivity, specificity and overall accuracy as compared to FDA approved bladder cancer biomarker Complement H. In another example, the biomarker may be indicative for late stage (T2/T3) bladder cancer. Table 9B and Table 12B show that the biomarker(s) of the present disclosure (when used either individually or in combination) provides better sensitivity, specificity and overall accuracy as compared to FDA approved Complement H. In yet another example, the biomarker may be indicative for early stage (Ta/T1) and late stage (T2/T3) bladder cancer. In one example, biomarkers that may be indicative, for late stage (T2/T3) of bladder cancer may include at least one of the biomarkers selected from the group consisting of coronin-1A, Apolipoprotein A4, semenogelin-2, gamma synuclein and DJ-1. That is, the biomarkers that may be indicative for late stage (T2/T3) bladder cancer may be one, two, three, four or all five of the biomarkers comprising coronin-1A, Apolipoprotein A4, semenogelin-2, gamma synuclein and DJ-1. In another example, the biomarkers that may be indicative for early stage (Ta/T1) bladder cancer may include the biomarker that is at least one selected from the group consisting of coronin-1A, DM, gamma synuclein, Apolipoprotein A4, and semenogelin-2. That is, the biomarkers that may be indicative for early stage (Ta/T1) bladder cancer may include one, two, three, four or all five of the biomarker comprising coronin-1A, DJ-1, gamma synuclein, and Apolipoprotein A4. In one example, all five biomarkers are selected and could advantageous to be used in detecting bladder cancer in patients because it addresses the fact that bladder cancers are extensively heterogeneous between individuals, not withstanding heterogeneity resulting from ethnicity and countries. For example, Example 2 of the present disclosure consistently demonstrated the superiority of the biomarker(s) of the present disclosure in detecting bladder cancer in subjects over control Complement H, which is known to be approved by the United States of America's Food and Drug Administrator (FDA) (see FIG. 6, FIG. 8, Table 9A, Table 9B, Table 12A and Table 12B). Furthermore, as illustrated in FIG. 6, the biomarker(s) of the present disclosure could be used for early detection of bladder cancer.

Figure 4:
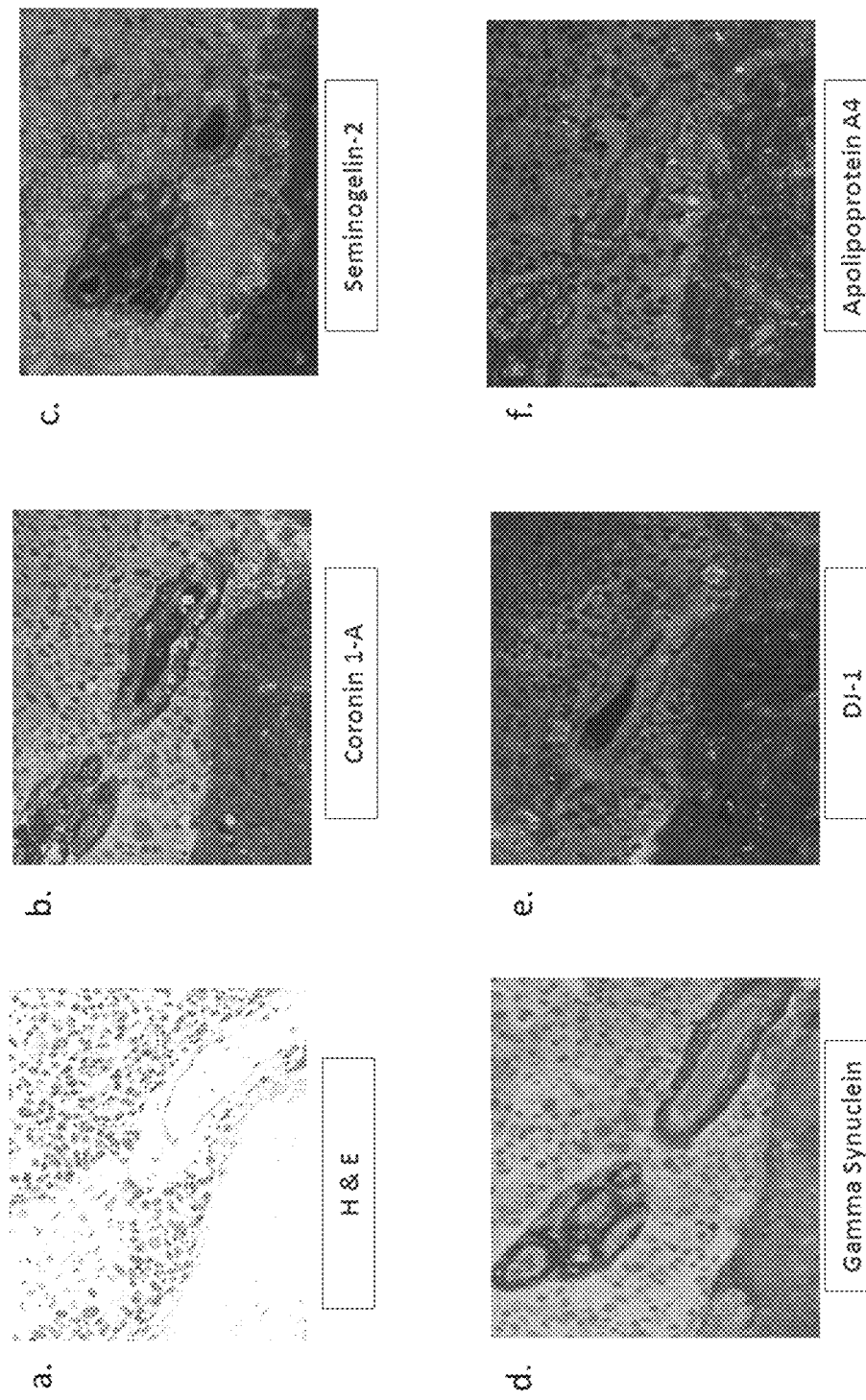
FIG. 4 is a collection of histological bladder specimen staining showing disordered proliferation of malignant urothelial cells (×20) in high grade bladder carcinoma, haematoxylin and eosin (H&E) staining (a), coronin 1-A (b), seminogelin-2 (c), gamma synuclein (d), DJ-1 (e), and Apolipoprotein A4 (f). Nuclei were counterstained with DAPI and are seen as light shade in this figure.

As illustrated in the Experimental Section of the present disclosure, the inventors of the present disclosure found that the biomarkers of the present disclosure may be detected in various sample types as described herein. For example, the biomarkers were clearly detected in tissue sections (e.g. histological sections shown in FIG. 14, FIG. 4) and urine samples (e.g. throughout the Experimental section, FIG. 6, FIG. 8, FIG. 9, FIG. 11, FIG. 1, FIG. 2, and FIG. 3). Thus, in one example of the present disclosure, the biomarkers of the present disclosure may be detected in a sample. For example, the sample may be tissue sections of biopsy material from all suitable organs such as the lung, the muscle, brain, liver, skin, pancreas, stomach, bladder and the like. In another example, the sample may include fluid samples derived from or comprising bodily fluids such as whole blood, serum, plasma, tears, saliva, nasal fluid, sputum, ear fluid, genital fluid, breast fluid, milk, colostrum, placental fluid, amniotic fluid, perspirate, synovial fluid, ascites fluid, cerebrospinal fluid, bile, gastric fluid, aqueous humor, vitreous humor, gastrointestinal fluid, exudate, transudate, pleural fluid, pericardial fluid, semen, upper airway fluid, peritoneal fluid, fluid harvested from a site of an immune response, fluid harvested from a pooled collection site, bronchial lavage, a nucleated cell sample, a fluid associated with a mucosal surface, hair, or skin, and urine. In one example, the fluid sample is urine or voided urine. The detection of the biomarkers of the present disclosure in urine is desirable as it allows for non-invasive detection of bladder cancer in patient. Example 2 of the Experimental Section also demonstrated that the biomarkers could also be used to predict or detect presence of bladder cancer in a patient who is also suffering from haematuria without compromising the specificity or accuracy of the detection.

In another aspect, it is envisaged that the biomarkers as described herein may be capable of diagnosing or detecting or predicting the likelihood of a patient or subject having bladder cancer. Accordingly, the biomarkers as described herein may be incorporated in diagnostic tools, detection systems, methods of diagnosis, methods of predicting or methods of determining the likelihood of a patient having bladder cancer.

In another aspect, there is provided a detection system. The detection system of the present disclosure may comprise a) a receiving section to receive a sample from a patient suspected to suffer from bladder cancer and wherein the sample is suspected to comprise one or more biomarkers of the present disclosure and b) a detection section comprising a substance or substances capable of detecting one or more biomarkers of the present disclosure. In one example, the sample may be a fluid sample, for example urine or a voided urine sample.

To assist in detecting the biomarkers of the present disclosure, the detection system of the present disclosure may comprise a substance capable of binding or specifically binding to one, two, three, four or all five biomarkers of the present disclosure. In one example, the substance may be biospecific capture reagents such as antibodies (or antigen-binding fragments thereof), interacting fusion proteins, aptamers or Affibodies (which are non-immunoglobulin-derived affinity proteins based on a three-helical bundle protein domain) that recognize the biomarker and/or variants thereof. In one example, the substance may be bound to a solid phase, wherein the biomarkers may be detected by mass spectrometry or by eluting the biomarkers from the biospecific capture reagents and detecting the eluted biomarkers by traditional MALDI or by SELDI. In another example, the detection system may be a biochip, test strip, or microtiter plate.

In one example, the antibodies may include antibodies known in the art to specifically recognise Coronin-1A, Apolipoprotein A4, Semenogelin II, gamma synuclein, or DJ-1. An example of antibodies that may be used to perform the present invention includes antibodies listed in Tables 8 and 2A below. In one example, the antibodies or antigen-binding fragments thereof may include anti-Coronin-1A antibody such as NB110-58867 (which recognises full-length recombinant human Coronin-1A expressed in and purified from E. coli. [UniProt# P31146], made by Novus Biologicals, USA); anti-apolipoprotein A4 antibody such as AB59036 (which recognises synthetic peptide: C-KEKESQDKTLSLP (SEQ ID NO: 13), corresponding to internal sequence amino acids 359-371 of Human APOA4 from Abcam, USA); anti-semenogelin II antibody such as AB108085 (which recognises synthetic peptide corresponding to a region within internal amino acids 42-91 (GQK-GQHYFGQKDQQHTKSKGSFSIQHTYHVDINDH-DWTRKSQQYDLNALH; SEQ ID NO: 14) of human Semenogelin II (NP_002999) from Abcam, USA); anti-gamma synuclein antibody such as AB55424 (which recognises synthetic peptide derived from human gamma Synuclein from Abcam, USA); anti-DJ-1 antibody such as SC-27006 (which was raised against a peptide mapping at the C-terminus of DJ-1 of human origin from Santa Cruz, USA) and NB100-483 (which recognises a synthetic peptide made to a C-terminal portion of the human Park7 protein (between residues 100-189) [UniProt Q99497] from Novus Biologicals, USA), and the like.

In another example, the detection system may be configured to detect one, two, three, four or all five biomarkers as described herein individually or in combination with one another.

In one example, the detection system may be used for predicting the risk of or diagnosing bladder cancer in a patient. As used herein, the term "predicting the risk" refers to assessing the probability of bladder cancer occurring in a subject.

In another aspect, there is provided a method of determining whether a patient suffers from or shows recurrence of bladder cancer or early stage bladder cancer or late stage bladder cancer. The method comprises detecting the presence of one or more biomarkers of the present disclosure.

As used herein, the term "patient" or "subject"- or "individual", which may be used interchangeably, relates to animals, for example mammals, including cows, horses, non-human primates, dogs, cats and humans. The patient of the present disclosure may be suspected of suffering or may have previously suffered from bladder cancer. For example, the method of the present invention may be applied to a subject suspected of suffering from bladder cancer. In another example, the method of the present disclosure may be applied to a subject suspected of having recurrence of bladder cancer. The term "recurrence" as used herein refers to the return of or redetection of bladder carcinoma in a patient who has been deemed to be free of bladder carcinoma.

In one example, when used in the method of the present disclosure, the biomarkers may be detected from samples, such as fluid sample. In one example, the fluid sample may be urine or voided urine. Advantageously, the specificity and sensitivity of the biomarkers as disclosed herein has permitted the detection system or method of the present disclosure to only require small urine volume, such as about 1 µl to about 30 ml. In one example, the urine sample may be about 1 µl, about 5 µl, about 10 µl, about 15 µl, about 20 µl, about 25 µl, about 30 µl, about 35 µl, about 40 µl, about 45 µl, about 50 µl, about 100 µl, about 150 µl, about 200 µl, about 250 µl, about 300 µl, about 350 µl, about 400 µl, about 450 µl, about 500 µl, about 550 µl, about 600 µl, about 650 µl, about 700 µl, about 750 µl, about 800 µl, about 850 µl, about 900 µl, about 950 µl, about 1 ml, about 2 ml, about 3 ml, about 4 ml, about 5 ml, about 6 ml, about 7 ml, about 8 ml, about 9 ml, about 10 ml, about 11 ml, about 12 ml, about 13 ml, about 14 ml, about 15 ml, about 16 ml, about 17 ml, about 18 ml, about 19 ml, about 20 ml, about 21 ml, about 22 ml, about 23 ml, about 24 ml, about 25 ml, about 26 ml, about 27 ml, about 28 ml, about 29 ml, to about 30 ml, or any values there between. As used herein, the term "about", in the context of amount of urine sample, typically means +/−5% of the stated value, more typically +/−4% of the stated value, more typically +/−3% of the stated value, more typically, +/−2% of the stated value, even more typically +/−1% of the stated value, and even more typically +/−0.5% of the stated value.

The biomarkers may be detected in samples, such as voided urine, using methods known in the art. It is appreciated that the person skilled in the art would understand which assays known in the art would be suitable in detecting the biomarkers of the present disclosure. For example, detection of the biomarkers of the present disclosure relates to the observance of presence or absence of the biomarkers. Detection can be done directly or indirectly. Direct detection relates to detection of the polypeptide based on a signal which is obtained from the polypeptide itself and the intensity of which directly correlates with the number of molecules of the polypeptide present in the sample. Such a signal—sometimes referred to as intensity signal may be obtained, e.g., by measuring an intensity value of a specific physical or chemical property of the polypeptide. Indirect measuring includes measuring of a signal obtained from a secondary component (i.e. a component not being the polypeptide itself) or a biological read out system, e.g., measurable cellular responses, ligands, labels, or enzymatic reaction products. For example, the detection may be carried out using molecular biological methods. The molecular biological methods may include, but are not limited to, polymerase chain reaction (PCR)—such as real time or quantitative PCR, Western Blot, Dot Blot, mass spectrometry, immunological methods, such as enzyme-linked immunosorbent assay (ELISA) using antibodies, and the like. For example, in the Experimental section of the present disclosure, Western Blot, Dot Blot, real time (RT) PCR and ELISA are used (see Examples 1 and 2).

Figure 12:
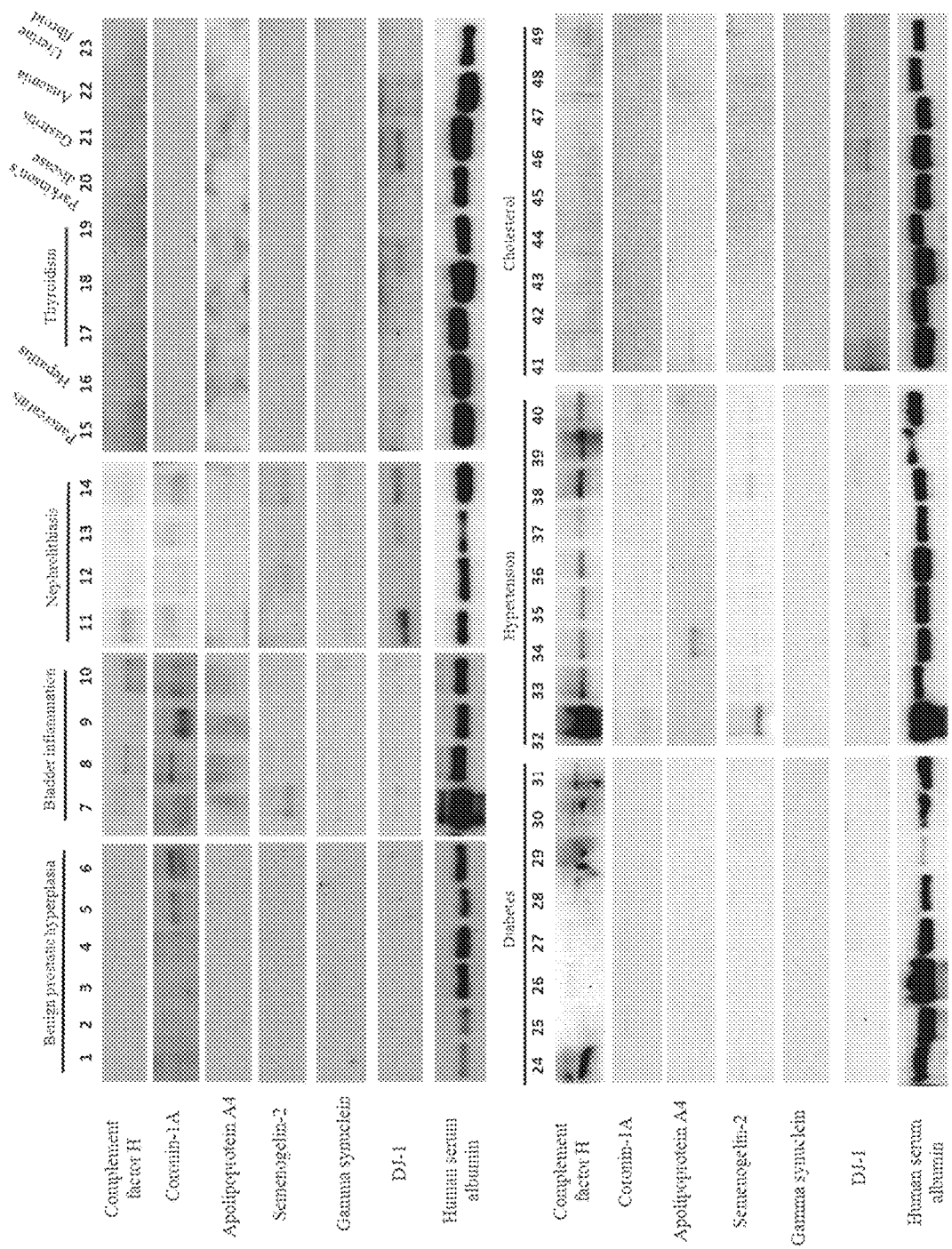
FIG. 12 shows Western Blot analysis comparing the expression of five biomarkers of the present disclosure (as well as control Complement factor H and human serum albumin, which was determined for each sample to establish whether there is a correlation between biomarker expression and haematuria) in urine samples obtained from 84 non-bladder cancer patients and patients suffering from diverse chronic ailments as described in Table 6.
Figure 12:
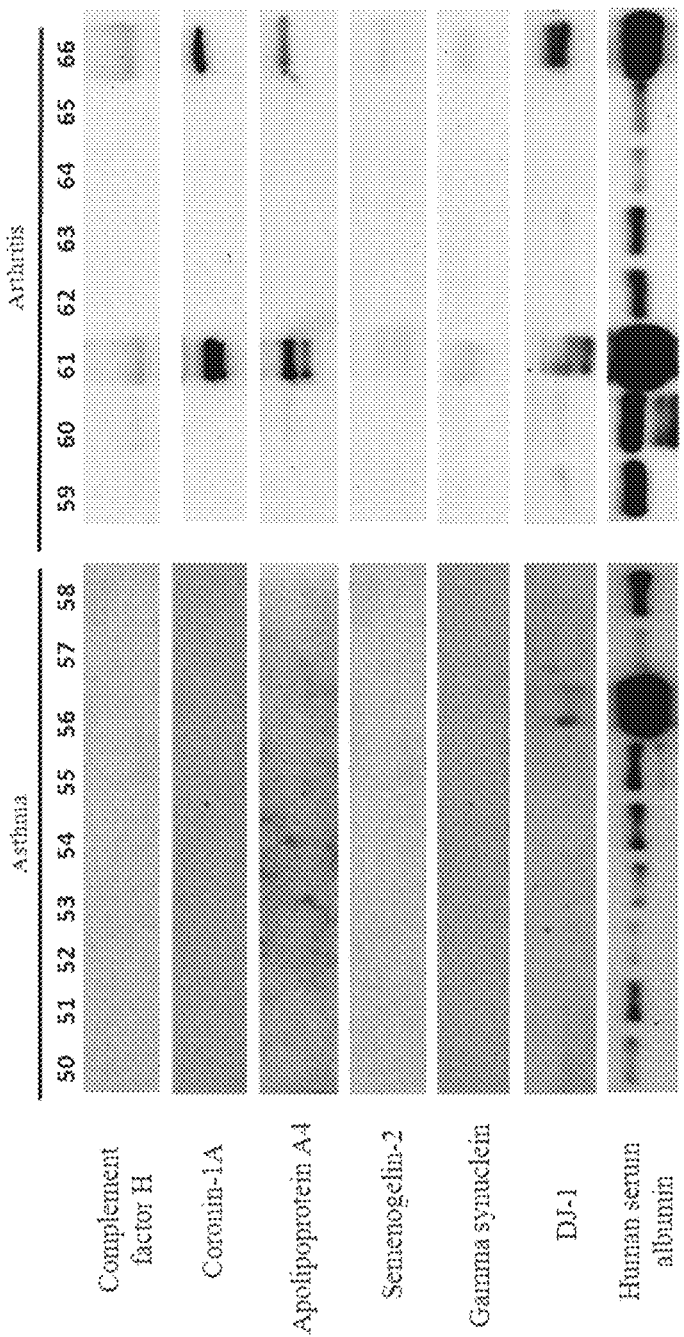

In one example, the indication as to whether the one or more biomarkers are present in a sample obtained from the patient may be made based on comparison of the results with a control group. For example, the method of the present disclosure may comprise a control group, which may include patients who do not suffer from bladder cancer. As demonstrated in FIG. 12 and FIG. 13, the biomarkers of the present disclosure is specific to bladder cancer such that the control group could be any patient who do not suffer from bladder cancer, including a patient who is healthy (i.e. do not have any known chronic diseases), a patient who has known chronic diseases but not cancer related, or a patient having cancer that is not bladder cancer.

In one aspect, there is provided a kit comprising a detection system as described herein and substances needed to carry out the method as described herein.

Also disclosed is a composition that may comprise the biomarkers of the present disclosure. In one example, the composition may be used in the detection system, method of determining or kit as described herein.

In one example, the biomarkers, methods, detection system or composition of the present disclosure may be useful in predicting outcome of bladder cancer in patients who may or may not be undergoing treatment or had received treatment for bladder cancer. The biomarkers, methods, detection system or composition of the present disclosure may also be useful in detecting or predicting recurrence in patients who may or may not be undergoing treatment or had received treatment for bladder cancer. In one example, the patient may have superficial bladder cancer (i.e. early stages such as non-muscle invasive, Ta/T1) who is treated with trans-urethral resection or who undergo Bacillus Calmette-Guerin (BCG) treatment.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXPERIMENTAL SECTION

Example 1

Example 1 Describes the Preliminary Study and Data on the Biomarkers of the Present Disclosure Materials (Clinical Specimens):

Voided urine samples and associated clinical information were collected in the conduct of the research following Institutional Review Board approval and informed consent (IRB #205-001; 2012-527-B). ~20 mL of voided urine was collected from healthy individuals and bladder cancer patients in urine collection and preservation tubes (Norgen Biotek Corporation, Cat #18118, USA). Voided urine samples were collected in three separate groups. The first group (cohort 1) consisted of 30 individuals with no previous history of urothelial cell carcinoma, gross haematuria, active urinary tract infection or urolithiasis. These specimens were served as control. The second group (cohort 2) consisted of 36 individuals with early phase of urothelial carcinoma (Ta or T1) and the third group (cohort 3) of 22 individuals with late phase of urothelial carcinoma (T2 or T3). Each urine aliquot was assigned a unique identifying number before laboratory processing. Urine proteins were enriched using a 3 kDa centrifugal filter as described by the manufacturer (Millipore, Carrigtwohill, Ireland). Briefly, 14 mL urine samples were centrifuged at 8000 g for 30 min at 4° C. Specimens with grossly visible blood were excluded. The samples were stored at −80° C. until further processing.

TABLE 1

Demographic and clinicopathologic characteristics of Normal/Non cancer and Cancer study cohort.

| | Normal/ Non-cancerous N = 30 | Bladder cancer patients N = 58 |
|---|---|---|
| Median age | | |
| Male:Female ratio | | |
| No. race: | | |
| Black | | |
| White | | |
| Others | | |
| Gross hematuria: | n/a | |
| Clinical stage | | |
| Ta/T1 | n/a | 36 |
| T2/T3 | n/n | 22 |

Methods

Mass Spectrometry Analysis

High resolution Mass Spectrometry (MS)-based quantitative proteomics approaches have been successfully used for quantitative comparison of the proteomes in two or more different conditions. The most commonly used methods for comparing and accurately quantifying protein levels rely on the use of differential isotopic labelling. A metabolic labelling method such as SILAC is applied only cell culture-based studies. Chemical labelling at proteins or peptide level (post-harvest stages) is amenable with any kind of protein samples including bio-fluids. Among these approaches Stable Isotope Reductive Dimethyl (R-diMe) labelling is a very straightforward, fast and inexpensive multiplex quantitative proteomics method that can quantify thousands of proteins in a single experiment using high resolution MS instruments such as LTQ-Orbitrap. An open source well-established MaxQuant program can be directly used to analyse R-diMe data. MaxQuant executes protein identification, relative ratios, ratio normalization to fix mixing errors and other relevant statistical information such as ratio significance.

Concentrated urine samples were suspended in 8M Urea, 100 mM ammonium bicarbonate (ABC, Sigma-Aldrich). The protein samples were reduced by adding 1M DTT to a final concentration of 5 mM DTT at room temperature for 30 min followed by alkylation with 10 mM iodoacetamide (IAA) in the dark for 30 min. Reduced samples were adjusted to 6 M urea and incubated with Lys-C (Promega)

(1:100) overnight at 37 C. After diluting the mixture to 1M Urea the sample were digested with Trypsin (porcine, modified sequencing grade; Promega) (1:50) at 37° C. for 4 h. The dimethyl labelling was performed as described in Hsu et al (Anal. Chem. 2003. 75, 6843-6852) with some modifications. The digest (peptide mixture) was acidified with 100 µl of 1% trifluoroacetic acid (TFA) before proceeding to dimethyl label on C18-SD solid phase extraction (SPE) cartridges (3M Empore™). The columns were first equilibrated with methanol, followed by 0.1% TFA/70% ACN and 0.1% TFA. The peptides were loaded onto three different columns followed by passing 'light' (45 mM sodium phosphate buffer pH 7.5, formaldehyde ($CH_2O$) (37% (vol/vol)), 'medium' (45 mM sodium phosphate buffer pH 7.5, formaldehyde ($CH_2O$) (20%, 98% D, Isotec), 0.3M sodium cyanoborohydride ($NaBH_3CN$) (Fluka)) and 'heavy' (45 mM sodium phosphate buffer pH 7.5, formaldehyde ($CH_2O$) (20%, 99% 13 C, 98% D, Isotec), 0.3M sodium cyanoborodeuteride ($NaBH_3CN$) (96% D, Sigma-Aldrich)) reagents through the columns. For forward labelling experiment "light", "medium" and "heavy" reagents were passed through Normal (Control), Ta/T1 and T2/T3 sample containing columns respectively. For reverse experiment "light", "medium" and "heavy" reagents were passed through T2/T3, Normal (Control) and Ta/T1 sample containing columns respectively. After washing with 0.1% TFA the labelled peptides were eluted with 0.1% TFA/70% ACN and mixed before concentrated using a speed vacuum concentrator. A small amount of the individual labelled peptides were subjected to label incorporation check by mass spectrometry analysis. The rest were mixed accordingly. IEF was performed on Agilent 3100 OFFGEL Fractionator (Agilent, G3100AA). Briefly, after rehydrating the 13 cm ImmobilineDryStrip pH 3-10 (Scimed) with a 12-well frame attached in a tray, the peptide mixture was loaded equally among the 12 wells. The 12-well frame was covered with a cover seal and electrodes were fixed onto the tray on wet electrode pads before attaching the tray onto the fractionator. Glycerol as cover fluid was added to the left and right electrode before running a total of 50 kVh with gradient. Collected fractions were desalted using C18 stage-tip as follows. 3 pieces of the solid phase extraction disks, C18 membrane discs (3M Empore) were packed into a 2000, pipette tip. The stage tips were conditioned first with methanol followed by 80% ACN/0.1% formic acid (FA) and 0.1% FA with centrifugation. During the conditioning, the flow rates of the stage tips were determined. Sample was then loaded onto the stage tip and centrifuged at the determined flow rate. The stage tip was then washed with 0.1% FA before peptides were eluted with 80% ACN/0.1% FA. Eluted peptides were concentrated in speed-vacuum concentrator for 15 min and topped up with 0.1% FA to a total volume of 20 µl before introducing into the mass spectrometer. Vacuum dried peptide samples were reconstituted in 0.1% formic acid and analysed using nanoHPLC (Proxeon, Thermo Scientific) coupled to a LTQ Orbitrap XL (Thermo FisherScientific). Peptides were trapped onto a C18 pre-column and separated on an analytical column using 2% acetonitrile/0.1% formic acid as Solvent A and 80% acetonitrile/0.1% formic acid as Solvent B. A 120 min gradient ranging from 5% to 50% solvent B, followed by a 5 min gradient ranging from 50% to 100% Solvent B at the flow rate of 250 nL/min was used. Survey full scan MS spectra (m/z 300-1400) were acquired with a resolution of r=60,000 at m/z 400, an AGC target of 1e6, and a maximum injection time of 500 ms. The ten most intense peptide ions in each survey scan with an ion intensity of >2000 counts and a charge state ≥2 were isolated sequentially to a target value of 1e4 and fragmented in the linear ion trap by collision-induced dissociation using a normalized collision energy of 35%. A dynamic exclusion was applied using a maximum exclusion list of 500 with one repeat count, repeat, and exclusion duration of 30 s. Data were searched using MaxQuant version 1.2.0.18 by uniprot DROME fasta (18787 sequences). Database searches were performed with trypsin cleavage site specificity allowing a maximum of two missed cleavages and two labelled amino acids as well as an initial mass tolerance of 7 ppm for precursor ions and 0.5 Da for fragment ions. Cysteine carbamidomethylation was searched as a fixed modification, and N-acetylation and oxidized methionine were searched as variable modifications. DimethylLys4, DimethylNter4, dimethylLys8, dimethylNter8 were selected as light and heavy labels respectively. Maximum false discovery rates were set to 0.01 for both protein and peptide. Proteins were considered identified when supported by at least one unique peptide with a minimum length of six amino acids.

RNA Isolation and Characterization

Total RNA was isolated from exfoliated cells of urine using ZR Urine RNA Isolation Kit, Cat# ZYR.R1039, CA, USA. 30 ml of voided urine pushed through a syringe into the ZRC GF™ Filter [provided with the kit] to isolate the exfoliated cells in the filter. The RNA was then purified following the manufacturer's instructions. RNA concentrations and A260/A280 ratios were measured with a NanoDrop®ND-1000 spectrophotometer. The purity of RNA was further quantified and stored at 80 or used for Real time PCR.

Real-Time PCR Analysis

Total RNA (500 ng) was reverse transcribed using SuperScript® III First-Strand Synthesis System, Invitrogen Cat#18080-051, CA, USA. RT-PCR preamplification reactions were carried out using EXPRESS SYBR® GreenER™ qPCR Supermix with Premixed ROX, Invitrogen, Cat#11794-01K, CA, USA. For each reaction/well 10 µL of the qPCR supermix was combined with 8 µL of each diluted cDNA sample and 2 µL of the primer resulting in a final volume of 20 µl. The primer sequences are the same as listed in Table 6 in Example 2, which are as follows: Coronin-$1A_F$ 5' CTTCAGCCGCATGAGTGAG 3' (SEQ ID NO: 3) and Coronin-$1A_R$ 5' AGGTAGACGATGTTGGTGTCA 3' (SEQ ID NO: 4); Apolipoprotein $A4_F$ 5' CCCAGCAACT-CAATGCCCT 3' (SEQ ID NO: 5) and Apolipoprotein $A4_R$ 5' CCTTCAGTTTCTCCGAGTCCT 3' (SEQ ID NO: 6); Semenogelin-$2_F$ 5' CCAACATGGACCCAAAGACAT 3' (SEQ ID NO: 7) and Semenogelin-$2_R$ 5' TGTACGT-GAAGACGGGTATGA 3' (SEQ ID NO: 8); Gamma synuclein$_F$ 5' CAAGAAGGGCTTCTCCATCGCCAAGG 3' (SEQ ID NO: 9) and Gamma synuclein$_R$ 5' CCTCTTTCTCTTTGGATGCCACACCC 3' (SEQ ID NO: 10); DJ-$1_F$ 5' TGCGTTCACTTTCAGCCT 3' (SEQ ID NO: 11) and DJ-$1_R$ 5' TGTGACTTCCATACTTCCGC3' (SEQ ID NO: 12). Thermal cycling conditions were as follows: Fast Real-Time PCR reaction; comprised of a 95° C. initial template denaturation, and 40 cycles of 95° C. denaturation and 60° C. anneal/extension. The reactions were carried out on a 7900HT Fast Real-Time PCR System (Applied Biosystems). The reactions were carried out on a 7900 HT Fast Real-Time PCR System (Applied Bio systems).

Western Blot Analysis

Urinary proteins were estimated using protein assay kit (Pierce™ BCA Protein Assay Kit, Cat #23225, Rockford, Ill., USA). Urine protein (100 µg) from individual samples was resolved on an SDS gel and transferred electrophoretically to a PVDF (polyvinylidene difluoride) membrane (Bio-Rad Laboratories, Cat #162-0177, CA, USA). The membrane was blocked with 5% BSA (Bovine Serum Albumin) in TBST (Tris-buffered saline containing 0.1% Tween-20) for 1 h at room temperature. The following primary antibodies were used for Western blot analysis listed in Table 2A. The membranes were probed by incubating first with primary antibody and then with horseradish peroxidase-conjugated secondary antibody, and developed using enhanced chemiluminescence detection (Immobilon Western Chemiluminescent HRP Substrate, EMD Millipore, USA).

TABLE 2A

Antibodies used in Western Blot and Dot Blot analysis

| Antibody name | Company | Catalogue No. | Dilution used | Secondary antibody |
|---|---|---|---|---|
| Anti-Factor H | Abcam | AB36134 | 1:500 | Goat |
| Coronin-1A | Novus Biologicals | NB110-58867 | 1:1000 | Rabbit |
| Anti-APOA4 | Abcam | AB59036 | 1:1000 | Goat |
| Anti-Semenogelin II | Abcam | AB108085 | 1:1000 | Rabbit |
| Anti-gamma Synuclein | Abcam | AB55424 | 1:1000 | Rabbit |
| DJ-1 | Santa cruz | SC-27006 | 1:500 | Goat |

Dot Blot Assay

Nitrocellulose membrane (BioTrace, Pall Gleman Laboratory, USA) was used for the assay. Grids were drawn by pencil to indicate the region to be blotted. Processed voided urine proteins (200 μg) from individual patients were spotted onto the nitrocellulose membrane at the centre of the grid. The area that the adsorbed solution was minimized by applying the sample slowly onto the membrane. The membrane was then left for one hour to dry. Non-specific sites on the membrane were blocked by soaking it in 5% BSA in TBS-T for 1 hr at RT. It was then incubated with primary antibody (1:100 to 1:10000 dilution range) dissolved in 5% BSA in TBS-T for 1 hr at RT followed by washing three times with TBS-T at 10 minutes interval. Incubation with HRP conjugated secondary antibody was made for 1 hour at RT followed by washing three times with TBS-T at 10 minutes interval. The membrane was incubated with ECL (Immobilon Western Chemiluminescent HRP Substrate, EMD Millipore, USA) and exposed for Chemiluminescence imaging Gbox.

Quantification by ELISA (Pierce 96-Well Plates-Corner Notch, Cat#15041, USA) (SuperBlock Blocking Buffer in TBS, Cat#37535, Thermo Fisher Scientific Inc., USA) (1-Step™ Ultra TMB-ELISA, Cat#34028, Thermo Fisher Scientific Inc., USA). Urinary protein concentration of each biomarker and Complement factor H was determined using respective ELISA kits (USCN Lifescience Inc., Wuhan, Hubei) according to the manufacturer's instructions (in triplicates). The kits are listed in Table 8. The biomarker quantity in the urine was normalized by loading an equal concentration of total protein into each well of the ELISA plate.

Histopathology and Immunostaining

A portion of each bladder biopsy samples were fixed in 10% NBF for 48 hours, transferred to 70% ethanol, and then embedded in paraffin. Samples were sectioned for 10 successive layers at 5-μm intervals and stained with hematoxylin and eosin for histopathological examination.

Immunohistochemical analysis was performed using formalin-fixed paraffin sections. Heat-induced epitope retrieval was performed using Bond™ Epitope Retrieval Solution 2 (for pH9) for 40 min at 100° C. The immunohistochemical staining was done using the Leica Bond™ Autostainers which uses their proprietary Bond™ Detection Refine Kit (Leica, cat no: DS9800) in their staining protocol. All immunofluorescence reactions were performed according to the antibodies dilutions listed in Table 2B. The secondary antibody, which is part of the detection kit, constitutes anti-rabbit poly-HRP-IgG containing 10% (v/v) animal serum in tris-buffered saline/0.9% ProClin™ 950. The solution is used undiluted.

TABLE 2B

Antibodies used in IHC

| Antibody name | Dilution used | IHC conditions |
|---|---|---|
| Coronin-1A | 1:500 | Rabbit |
| Anti-APOA4 | 1:250 | Rabbit |
| Anti-Semenogelin II | 1:250 | Rabbit |
| Anti-gamma Synuclein | 1:500 | Rabbit |
| DJ-1 | 1:500 | Rabbit |

Mass Spectrometric Analysis of Urinary Proteins: Stable Isotope Reductive Dimethyl Labelling High resolution Mass Spectrometry (MS)-based quantitative proteomics approaches have been successfully used for quantitative comparison of the proteomes in two or more different conditions. The most commonly used methods for comparing and accurately quantifying protein levels rely on the use of differential isotopic labelling, either by metabolically or chemically. Metabolic labelling methods such as SILAC can directly be applied to only cell culture-based studies. Chemical labelling at proteins or peptide level is amenable with any kind of protein samples including biofluids. Among these approaches Stable Isotope Reductive Dimethyl (R-diMe) labelling is a very straightforward, fast and inexpensive multiplex quantitative proteomics method that can quantify thousands of proteins in a single experiment using high resolution MS instruments such as LTQ-Orbitrap. An open source well-established MaxQuant program can be directly used to analyse R-diMe data. Triple labelled R-diMe analysis was carried out for concentrated urine samples from normal (Control), Ta/T1 and T2/T3 patients. Samples were digested using Lys-C followed by Trypsin using standard procedures. In order to reduce sample complexity resulting peptide mixture (from differentially labelled urine samples) was fractionated using isoelectric focusing electrophoresis on Agilent 3100 OFFGEL Fractionator. Each fraction was subjected to nanoHPLC (Proxeon, Thermo Scientific)-LTQ Orbitrap mass spectrometry analysisRaw data were processed using MaxQuant version 1.2.0.18 by uniprot DROME fasta (18787 sequences). DimethylLys4, DimethylNter4, dimethylLys8, dimethylNter8 were selected as light, medium and heavy labels respectively. Maximum false discovery rates were set to 0.01 for both protein and peptide. Proteins were considered identified when supported by at least one unique peptide with a minimum length of six amino acids.

The lists of identified proteins were further analysed using various immunochemical techniques. From the discovery phase, 17 candidates were picked to check their abundance in individual urine samples from early and late stage bladder cancer patients. The relative ability and affluence of each biomarker were assessed in Western blot, RT-PCR and Dot blot. From the present study, five candidate biomarkers were selected for bladder carcinoma detection, both individually and in combinations. In addition levels of individual biomarker were monitored in urine samples using commercial enzyme-linked immunosorbent assays (ELISA). Calibration curves were prepared using purified standards for each protein assessed. The diagnostic value of the five biomarkers for BCa detection was determined. A logistic regression procedure was applied with bladder carcinoma status as the response variable and the biomarkers as predictive variables. Once the predictive model was generated, Receiver operating characteristics (ROC) curves were generated using Graphpad Prism® providing plots of the value for sensitivity against the false-positive rate. The relative ability of the different combination of our selected biomarkers was estimated by calculating the area under the ROC curves (AUC) using Graphpad Prism®. Higher AUC indicating a stronger predictor. Thresholds for each biomarker were selected based on maximum Youden's Index. Sensitivity, specificity, positive predictive value (PPV), negative predictive value (NPV), and overall accuracy were subsequently computed using the selected threshold for diagnosis.

Results

Assessment of Comparative Analysis of Urine Proteome in the Bladder Cancer Biomarker Discovery First qMS analysis was performed on urine samples that were prepared by pooling equal volumes of urine samples from four volunteers as described in methods. In order to minimize experimental errors, biological (different pools) and technical replicates (different labelling as well as different MS runs for the same samples) were included. Finally all dataset were combined to obtain average fold changes of the proteins present in urine samples. Any proteins with two or more fold changes in comparison to normal urine sample were considered as over-secreted proteins (Table 3).

TABLE 3

Number of urinary markers detected in each patient group

| Stages in Bladder Cancer | Number of Urinary markers detected |
|---|---|
| Only Ta/T1 (non-muscle invasive) | 87 |
| Only T2/T3 (muscle-invasive) | 56 |
| Both Ta/T1 and T2/T3 | 45 |

Figure 11:
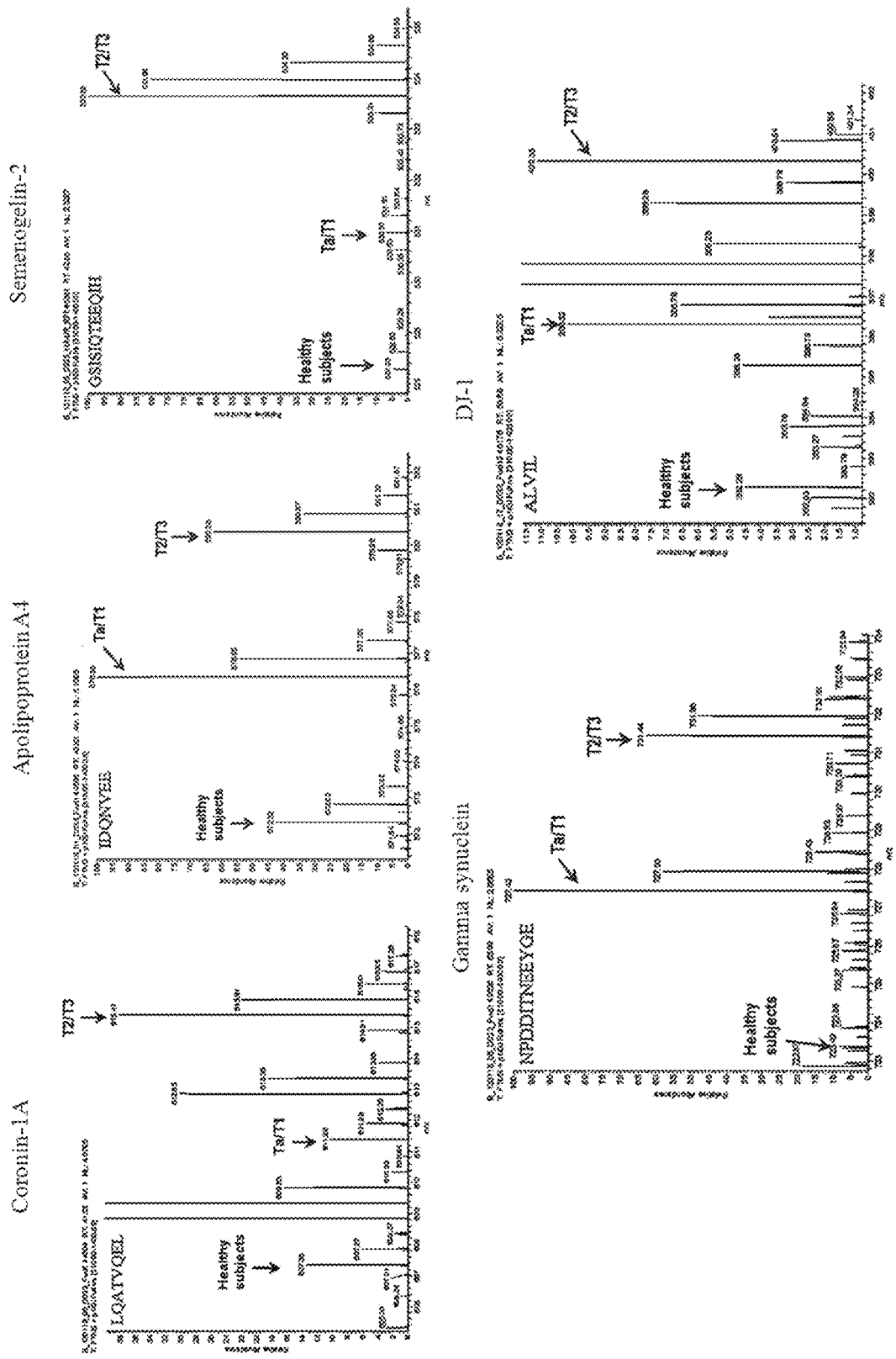
FIG. 11 is a representative mass spectra showing quantification of the selected biomarkers in healthy, non-muscle invasive (Ta/T1) and muscle invasive (T2/T3) bladder carcinoma sample.

From this list of proteins, 17 potential candidates were selected for initial validation, based on their function, subcellular localization and disease association. Different biochemical techniques were applied to validate these selected markers: RT-PCR was used to quantify the mRNA expression of the identified hits and Western Blotting was used to check the expression levels of selected biomarkers. Based on the results of the mRNA expression analysis five candidate biomarkers were shown to have elevated level of their mRNA expression in both non-muscles invasive as well as muscle invasive BC patients compared to normal individuals. Fold change for RNA expression for Coronin-1A, Apolipoprotein A4, Semenogelin-2, Gamma Synuclein and DJ-1 showed a range of expression. Most importantly all the markers exhibited a high level of fold change compared to a normal individual. These data were further compared with FDA approved BTA-TRAK assay factor, complement H (FIG. 1). The gene level data were compared with our MS data. Representative MS spectra of above potential markers also clearly showed the presence of their higher levels in patients' samples (FIG. 11)

Coronin-1A, Apolipoprotein A4, Semenogelin-2, Gamma Synuclein and DJ-1 levels were then analysed in pooled urine samples (FIG. 2A) and 24 urine samples from individual non-muscle invasive BC patients (FIG. 2B, FIG. 3) and 24 urine samples, for muscle invasive BC patient samples (FIG. 2C) by Western Blotting. After normalization, the relative protein levels of the five candidate proteins showed elevated level of expression are listed in Table 4. The data obtained by Western blot analyses and RT-PCR matched.

TABLE 4

Western blot analysis

| Biomarkers | Total no. of Ta/T1 samples used | % positivity | Total no. of T2/T3 samples used | % positivity |
|---|---|---|---|---|
| Complement H | 24 | 66.7 | 14 | 85.7 |
| Coronin-1A | 24 | 79.2 | 14 | 98.9 |
| Apolipoprotein A4 | 24 | 79.2 | 14 | 98.9 |
| Semenogelin-2 | 24 | 62.5 | 14 | 71.4 |
| Gamma synuclein | 24 | 54.2 | 14 | 71.4 |
| DJ-1 | 24 | 70.8 | 14 | 85.71 |

A simple non-invasive rapid-based dot blot assay was also developed for the detection of five discovered markers in urine samples of patients with bladder cancer. This technique allows a semi quantitative reading of the resulting coloured dot, if the marker is detected and forms a ring (i.e. a positive test). A colourless dot or no ring formation was produced if no marker was detected (i.e. a negative test) listed in FIG. 3 In all assays, all data generated by the biomarkers of the present disclosure is compared with the FDA-approved BTA-TRAK assay factor, complement H.

To further evaluate the diagnostic performance of the biomarkers of the present disclosure, their expressions were checked in biopsy samples acquired for high grade bladder cancer patients. Immunohistology was performed for all five biomarkers. The result clearly confirmed the positive staining of all five biomarkers in the tissue sections shown in FIG. 4.

Advanced MS-based isotope dimethyl labelling approach was designed to identify a panel of novel biomarkers. This method is a very straightforward, fast and inexpensive multiplex quantitative proteomics approach based on efficient chemical labelling that enables quantitative comparison of the proteomes of bio-fluids. In this study, urine samples were used combined with multiplex quantitative proteomics method using high resolution MS instruments such as LTQ-Orbitrap to analyse the differences between the bladder cancer patients and normal individuals. The Mass Spectrometry studies performed in the present disclosure obtained a list of proteins elevated in early phase Ta/T1, late phase T2/T3 and both Ta/T1 and T2/T3 of bladder cancer (not shown).

Figure 5:
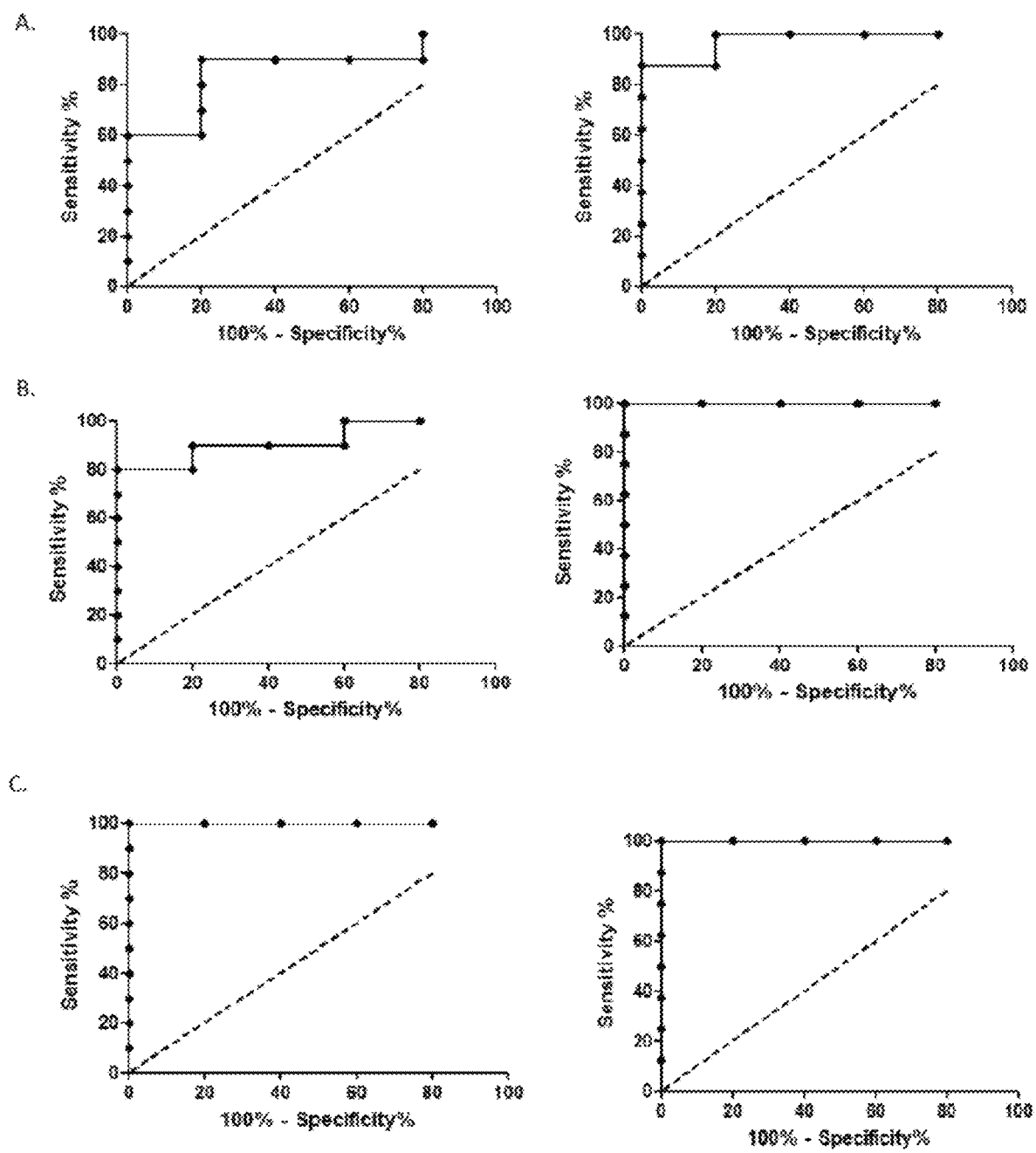
FIG. 5 is a diagnostic representation of five biomarkers in various combinations. ROC graphs were plotted to compare data collected from A. 5-biomarker combination (Coronin-1A, Apolipoprotein A1, semenogelin-2, gamma synuclein and DJ-1); B. 4-biomarker combination (Coronin-1A, Apolipoprotein A1, semenogelin-2, and gamma synuclein); C. 3-biomarker combination (Coronin-1A, Apolipoprotein A1, and semenogelin-2); D. BTA-TRAK test. Based on the area under the ROC curve (AUROC), Youden's Index cut-off values, which maximized the sum of sensitivity and specificity, were determined for each biomarker and biomarkers in combinations.
Figure 5:
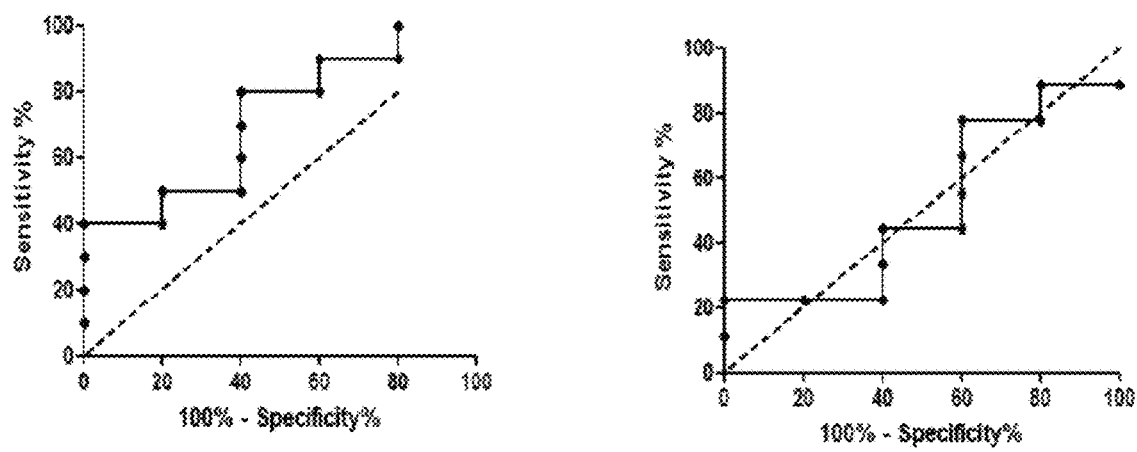

Following filtering procedures based on importance and relevance, 17 markers were selected and further narrowed down to five potential markers following mRNA expression and Western Blot studies. These five biomarkers were further validated by Dot Blot and ELISA techniques, confirming that they can be used as non-invasive markers. Data collected from the present studies were statistically analysed to generate the specificity and sensitivity of the biomarkers. The biomarker panel of the present disclosure (Coronin-1A, Apolipoprotein A4, Seminogelin-2, Gamma synuclein, DJ-1/PARK 7) executed the most accurate multi-analytebased assay for BC detection in the 88 subject cohort. The incorporation of additional biomarkers is likely to affect specificity and sensitivity. Testing all possible combinations, it was found that three of the five biomarker panel (Coronin-1A, ApoA4 and Gamma synuclein) combination yielded an overall accuracy of 100% and hold both high sensitivity (100%) and specificity (100%) (FIG. 5). Thus, Example 1 suggests that three biomarkers combination may provide reliable diagnosis of non-muscle invasive and muscle invasive bladder carcinoma (Table 5). To validate this finding, further studies with larger sample size was conducted in Example 2 below.

TABLE 6

Patient Details (n = 365)

| Sample type | No. of samples | Clinical stages | Disease types/origin of cancers | Volume collected |
|---|---|---|---|---|
| Healthy Subjects | 30 | n/a | n/a | 20 ml for initial screening and 5 ml for validation phase |
| Bladder Cancer | 72 | Ta/T1 | bladder carcinoma | |
| | 55 | T2/T3 | | |

TABLE 5

Performance values for individuals and three different combinations.

| Biomarkers | AUROC | Cut-off value (ng/ml) | Sensitivity % | Specificity % | Positive predictive value (PPV) % | Negative predictive value (NPV) % | Overall accuracy % |
|---|---|---|---|---|---|---|---|
| BTA TRAK (Complement H) | 0.96 | 4.952 | 90 | 100 | 100 | 83.33 | 93.33 |
| Coronin-1A | 1 | 15.4872 | 100 | 100 | 100 | 100 | 100 |
| Apolipoprotein A4 | 0.84 | 4.1468 | 90 | 80 | 90 | 80 | 86.67 |
| Semenogelin-2 | 1 | 6.9548 | 100 | 100 | 100 | 100 | 100 |
| Gamma synuclein | 0.66 | 3.7321 | 60 | 80 | 85.71 | 50 | 66.67 |
| DJ-1 | 0.72 | 392.35 | 80 | 60 | 80 | 60 | 73.33 |
| All five biomarkers | 0.86 | 0.9237 | 90 | 80 | 90 | 80 | 86.67 |
| Four biomarkers | 0.92 | 1.106 | 80 | 100 | 100 | 71.43 | 86.67 |
| Best three biomarkers | 1 | 0.8927 | 100 | 100 | 100 | 100 | 100 |

Example 2

Example 2 is a Continuation and Updated Study of Example 1, where Essentially the Same Experiments (on Larger Sample Size) were Conducted to Validate the Reliability of the Biomarkers of the Present Disclosure Materials and Methods Urine Samples Voided urine samples and associated clinical information (Table 6) were collected following Institutional Review Board approval and informed consent. For the initial screening, 20 ml of voided urine was collected from healthy subjects and bladder carcinoma patients in preservation tubes and stored at −80° C. (Norgen Biotek Corporation, Canada). Three separate groups were constituted: the control group, corresponding to healthy subjects with no previous history of urothelial cell carcinoma, gross haematuria, active urinary tract infection or urolithiasis; a second group, formed by Ta and T1 bladder carcinoma patients, characterized as having non-muscle invasive bladder carcinoma; and a third group, comprising T2 and T3 bladder carcinoma patients, characterized as having muscle invasive bladder carcinoma. Each urine aliquot was assigned a unique identifying number before laboratory processing. Urine samples with significant blood contamination, as determined by visual inspection or based on the Dip-stick urine test (Combur9, Roche Diagnostics, Basel, Switzerland) were excluded. Samples were stored at −80° C. until further processing.

TABLE 6-continued

Patient Details (n = 365)

| Sample type | No. of samples | Clinical stages | Disease types/origin of cancers | Volume collected |
|---|---|---|---|---|
| Chronic Ailment | 120 | n/a | Diabetes, hypercholesterolemia, hypertension, benign prostatic hyperplasia, bladder inflammation, nephrolithiasis, pancreatitis, hepatitis, arthritis, asthma, thyroidism, Parkinson's disease, gastritis, anaemia, uterine fibroids. | 5 ml |
| Various Cancer Types | 88 | n/a | Lung, prostate, breast, gastric, colon, endometrium, uterus, pancreas, peritoneum, parotid, tongue, thyroid gland, kidney. | 5 ml |

Abbreviation:
n/a, not applicable;
BCa, bladder carcinoma.

For validation screens, an additional 5 ml of voided urine was collected from patients affected by chronic diseases, bladder carcinoma and other cancer types.

Quantitative Mass Spectrometry Analysis of Urine Samples

Urine proteins were concentrated using a 3 kDa centrifugal filter according to the manufacturer's instructions (Millipore, Carrigtwohill, Ireland). Four samples from each cohort, i.e., healthy, Ta/T1 and T2/T3 bladder carcinoma stage, were pooled and centrifuged at 8000×g for 30-60 min at 4° C. Acetone-precipitated samples were reconstituted in 120 µl of 8 M urea in 100 mM ammonium bicarbonate.

Samples were reduced by the addition of 1 M of dithiothreitol to a final concentration of 5 mM in each sample, and then incubated at room temperature for 30 min. Alkylation was performed by the addition of 0.5 M of iodoacetamide to a final concentration of 10 mM and the samples were incubated in the dark for 30 min. All samples were then diluted from the initial 8 M urea to 6 M urea using 100 mM ammonium bicarbonate and then incubated with Lys-C (enzyme-to-protein ratio of 1:100) at 37° C. overnight. Digestion mixtures were adjusted to a final concentration of 1 M urea by the addition of 50 mM ammonium bicarbonate followed by incubation with trypsin (enzyme-to-protein ratio of 1:50) at 37° C. for 4 h.

The tryptic peptide mixtures were subjected to on-column stable isotope dimethyl labelling as described by Swa, H. L., A. A. Shaik, et al. (2014). "Mass spectrometry-based quantitative proteomics and integrative network analysis accentuates modulating roles of Annexin-1 in mammary tumorigenesis." Proteomics. Using a triple-labelling approach. Differentially labelled urine samples were mixed and fractionated using isoelectric focusing electrophoresis on an Agilent 3100 OFFGEL Fractionator (12 fractions). The samples were cleaned up using self-packed C18 stage tips and subjected to mass spectrometry analysis, as previously described (Swa, Shaik et al. 2014). Raw data were processed with MaxQuant version 1.3.0.5 using the 2013-07_uniprot human fasta database (88354 entries). Maximum false discovery rates were set to 0.01 for both protein and peptide. Proteins were considered identified when supported by at least one unique peptide with a minimum length of seven amino acids.

Quantitative Real-Time Polymerase Chain Reaction

Total RNA was isolated from sloughed cells within the 5 ml urine samples using ZR Urine RNA Isolation Kit (Zymo Research, Irvine, Calif.). Total RNA (500 ng) was reverse transcribed using SuperScript® III First-Strand Synthesis System (Invitrogen, Carlsbad, Calif.). RT-PCR pre-amplification reactions were carried out using EXPRESS SYBR® GreenER™ qPCR Supermix with Premixed ROX (Invitrogen). The primer sequences are listed in Table 7.

TABLE 7

Primer sequences for quantitative reverse transcription polymerase chain reaction (q RT-PCR)

| Genes | Forward sequence (5'→3') | SEQ ID NO: | Reverse sequence (5'→3') | SEQ ID NO: |
|---|---|---|---|---|
| Complement factor H | CACACAAGATGG ATGGTCGC | 1 | GGATGGCAGGCAA CGTCTAT | 2 |
| Coronin-1A | CTTCAGCCGCAT GAGTGAG | 3 | AGGTAGACGATGT TGGTGTCA | 4 |
| Apolipo-protein A4 | CCCAGCAACTCA ATGCCCT | 5 | CCTTCAGTTTCTC CGAGTCCT | 6 |
| Semenogelin-2 | CCAACATGGACC CAAAGACAT | 7 | TGTACGTGAAGAC GGGTATGA | 8 |
| Gamma synuclein | CAAGAAGGGCTT CTCCATCGCCAA GG | 9 | CCTCTTTCTCTTT GGATGCCACACCC | 10 |
| DJ-1 | TGCGTTCACTTT CAGCCT | 11 | TGTGACTTCCATA CTTCCGC | 12 |

Western Blot Analysis

Western blot was carried out on urine samples after they were centrifuged to eliminate cells. Protein concentrations were estimated using a BCA Protein Assay Kit (Pierce, Rockford, Ill.). Proteins (100 μg) from individual samples were resolved on sodium dodecyl sulphate (SDS) polyacrylamide gels and transferred electrophoretically to polyvinylidene difluoride (PVDF) membranes (Bio-Rad Laboratories, Hercules, Calif.). Membranes were blocked with 5% bovine serum albumin (BSA) in Tris-buffered saline containing 0.1% Tween-20 (TBST) for 1 h at room temperature followed by probing with primary antibodies listed in Table 8.

TABLE 8

Antibodies and ELISA kits used for Western Blot, immunostaining and ELISA assays

| Biomarkers | Catalogue no. for antibodies used | Western blot (Antibody dilution used) | Immuno-histochemistry (Antibody dilution used) | ELISA kits catalogue no. | ELISA detection range |
|---|---|---|---|---|---|
| Coronin-1A | NB110-58867 | 1:5000 | 1:200 | SEJ355Hu | 0.313-20 ng/ml |

TABLE 8-continued

Antibodies and ELISA kits used for Western Blot, immunostaining and ELISA assays

| Biomarkers | Catalogue no. for antibodies used | Western blot (Antibody dilution used) | Immuno-histochemistry (Antibody dilution used) | ELISA kits catalogue no. | ELISA detection range |
|---|---|---|---|---|---|
| Apolipoprotein A-IV | ab59036 | 1:1000 | 1:200 | SEB967Hu | — 78.13-5000 pg/ml |
| Semenogelin-2 | ab108085 | 1:1000 | 1:200 | SEH184Hu | — 0.313-20 ng/ml |
| Gamma-synuclein | ab55424 | 1:1000 | 1:200 | SEA939Hu | — 0.313-20 ng/ml |
| DJ-1 | NB100-483 | 1:1000 | 1:200 | SEL059Hu | — 15.63-1000 pg/ml |
| Complement factor H | ab36134 | 1:500 | — | SEA635Hu | — 23.44-1500 ng/ml |

Protein Quantification by ELISA

Urinary protein concentration of each biomarker (Coronin-1A, Apolipoprotein A4, Semenogelin-2, Gamma synuclein and DJ-1) as well as that of the FDA approved Complement factor H was determined using respective ELISA kits (Table 8) (USCN Lifescience Inc., Wuhan, Hubei). The assays were performed according to the manufacturer's instructions. All tests were performed in triplicate. The biomarker quantity in the urine was normalized by loading an equal concentration of total protein into each well of the ELISA plate. Readings were performed at 450 nm in an automatic micro-plate reader Infinite® M1000 PRO (Tecan, Mannedorf, Switzerland).

Histopathology

Bladder carcinoma biopsy samples were fixed in 10% neutral-buffered formalin (NBF) for 48 h, transferred to 70% ethanol, and then embedded in paraffin. Four-µm tissue sections were stained with hematoxylin and eosin for histopathological examination. Heat-induced epitope retrieval was performed using Bond™ Epitope Retrieval Solution 2 (for pH 9.0) for 40 min at 100° C. Immunohistochemical staining was done using the Leica Bond™ Autosiainer, which uses their proprietary Bond™ Detection Refine Kit (Leica, Solms, Germany). All immunofluorescence labelling was performed using antibody dilutions listed in Table 8.

Statistical Analysis

All data were analysed using GraphPad Prism® 5.0 software. For RT-PCR data, significant differences or fold-change in biomarker expression among healthy subjects, Ta/T1 and T2/T3 patients were accessed using two-sided Mann Whitney U-test. Western blotting data intensity was quantified using the image processing program ImageJ (National Institute of Health, Bethesda, Md.). Pearson correlation test was conducted for any association of the biomarkers with blood plasma. The diagnostic model combining of the five biomarkers was developed using the Lasso regression model from Matlab® R2012a statistical toolbox version 8.0 (MathWorks, Natick, Mass.). Calibration curves were prepared using purified proteins provided with the ELISA kits. Receiver Operating Characteristic (ROC) curves and AUC were constructed using Graphpad Prism® (GraphPad Software, La Jolla, Calif.). Higher AUC ($>0.5$) indicated a stronger predictor than random chance. Thresholds for each biomarker were selected based on Youden's Index, J=sensitivity+specificity−1. Sensitivity, specificity, positive predictive value (PPV), negative predictive value (NPV), and overall accuracy were computed using the selected threshold for diagnosis. A p-value of $p<0.05$ (two-sided) was regarded as significant.

Results

Candidate Biomarker Identification for Bladder Carcinoma Detection Using Quantitative MS To identify potential biomarkers for the diagnosis of non-muscle invasive (Ta/T1) and muscle invasive bladder carcinoma (T2/T3), MS analysis was performed using pooled urine samples from four volunteers of equal volumes. In order to minimize experimental errors, biological (different pools) and technical replicates (different labelling as well as different MS runs for the same samples) were included. Finally, the entire dataset was combined to obtain the mean fold change in proteins present in bladder carcinoma urine samples as compared with healthy urine samples. Proteins with a two-fold or higher change with at least two ratio counts (at least in one stage) were considered as over-secreted proteins as compared with samples from healthy subjects. The over-secreted proteins were scrutinized through extensive online database literature searching and were shortlisted based on their novelty, previously published cancer association, and subcellular localization.

Biomarker mRNA Fold Change in Sloughed Cells of Voided Urine

Figure 8:
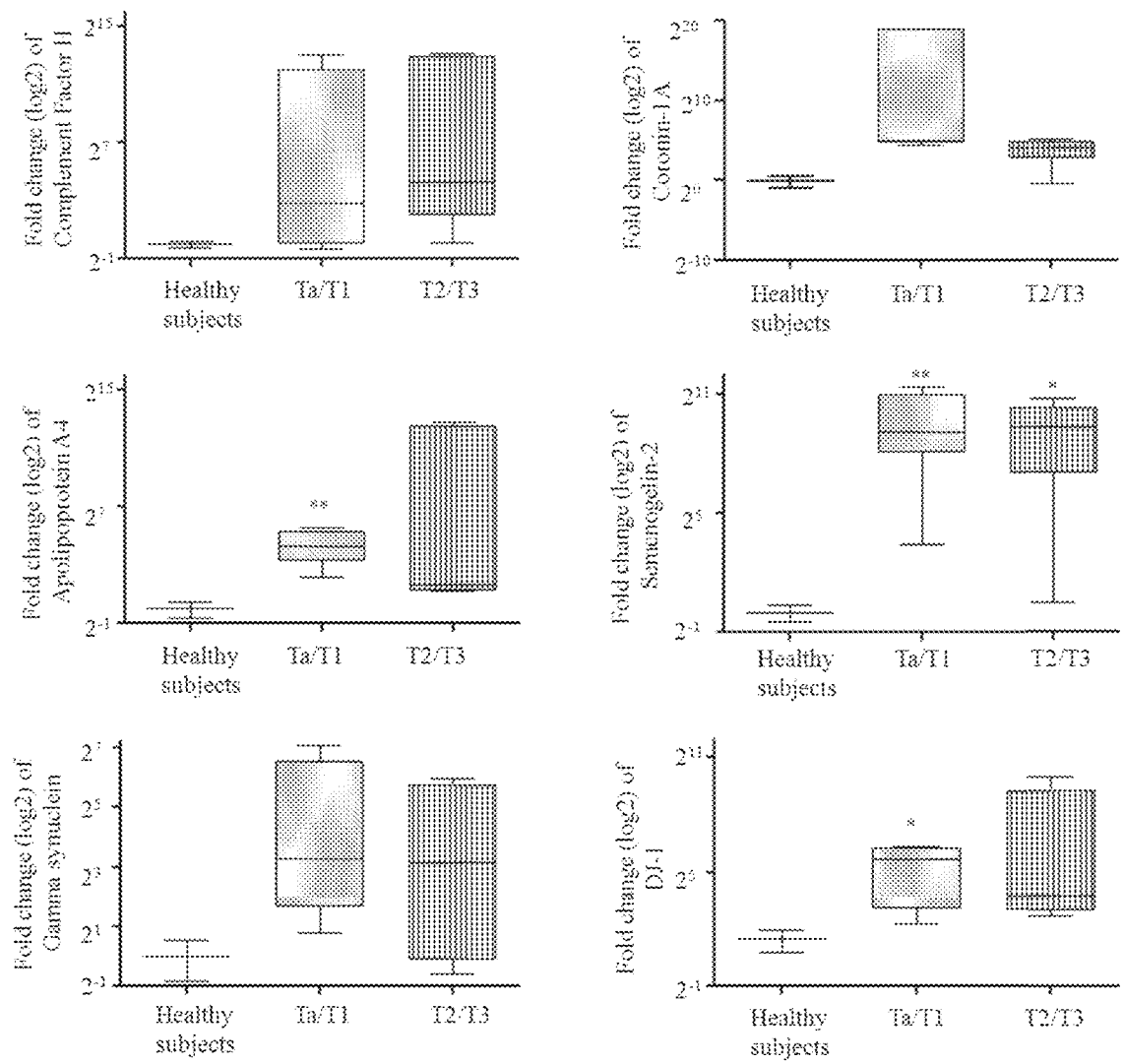
FIG. 8 shows a box and whiskers plot of mRNA expression analysis using RT-PCR of the five biomarkers of the present disclosure (as well as control Complement factor H) in normal healthy subjects (n=2), patients with Ta/T1 (non-muscle invasive; NMI; n=5) bladder carcinoma and patients with T2/T3 (muscle invasive; MI; n=5) bladder carcinoma. The biomarker Ct values have been normalized to β-Actin endogenous control. p value for comparison to normal: *$p<0.05$, $p<0.01$, *$p<0.001$.

Shortlisted potential biomarkers were considered for initial validation by RT-PCR with ten samples for each of the three groups: control group (healthy subjects), Ta/T1 bladder carcinoma (non-muscle invasive) group; and T2/T3 bladder carcinoma (muscle invasive) group. Based on the results of the mRNA expression analysis, five candidate biomarkers—Coronin-1A, Apolipoprotein A4, Semenogelin-2, Gamma Synuclein and DJ-1—had a significantly higher fold change in expression in non-muscle invasive (Ta/T1) and muscle invasive (T2/T3) bladder carcinoma patients as compared to that in healthy subjects. Complement factor H also exhibited higher mRNA expression in the urine of bladder carcinoma patients (FIG. 8).

Figure 7:
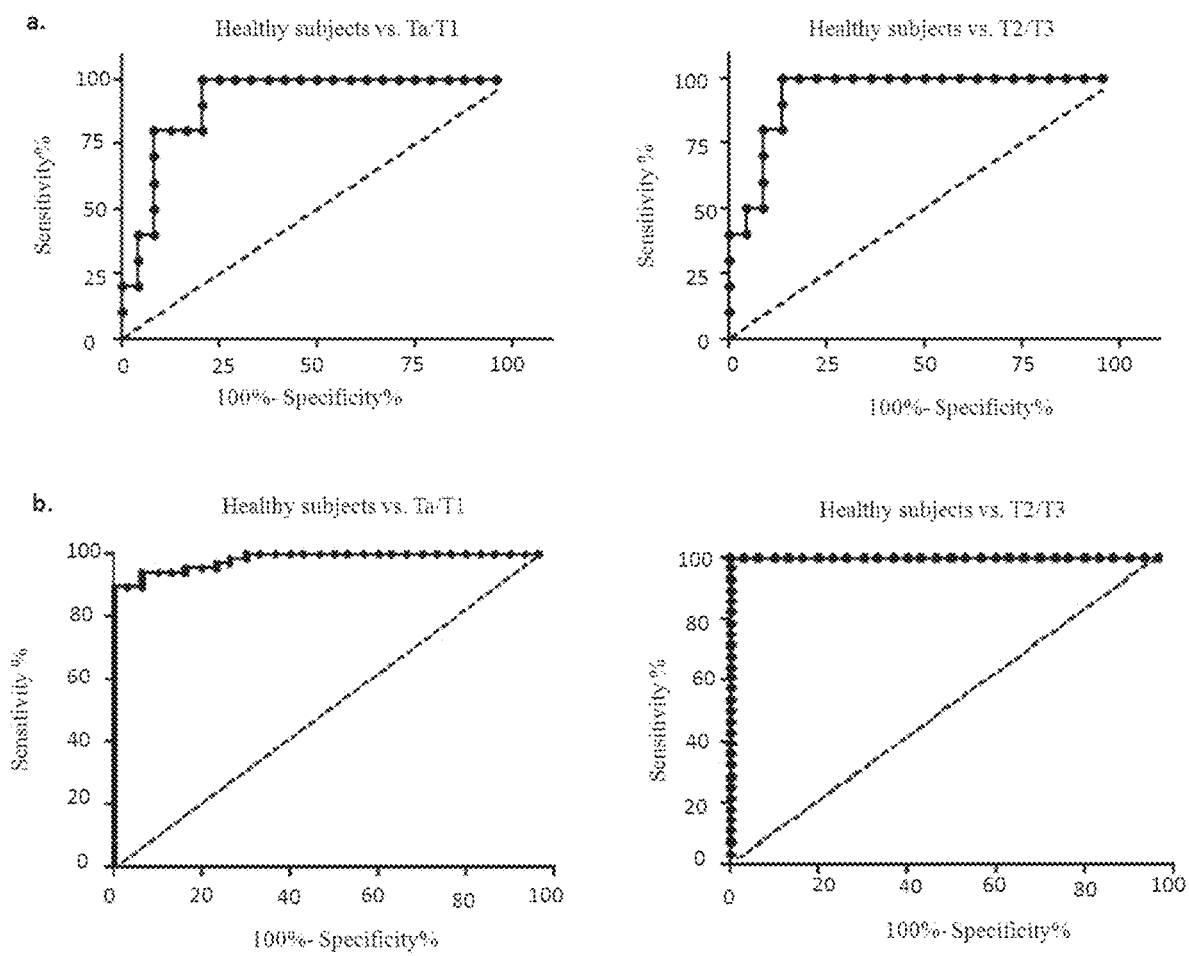
FIG. 7a shows a Receiver Operating Characteristic (ROC) graph illustrating the overall diagnostic accuracy of ELISA using the biomarkers of the present disclosure in patients with Ta/T1 (non-muscle invasive) bladder carcinoma with healthy subjects and patients with T2/T3 (muscle invasive) bladder carcinoma with healthy subjects. This model assesses the biomarker efficiency to distinguish both non-muscle invasive (NMI; Ta/T1) and muscle invasive (MI; T2/T3) bladder carcinoma from healthy subjects based on data obtained from ELISA analysis.
FIG. 7b shows a Receiver Operating Characteristic (ROC) graph illustrating the overall diagnostic accuracy of Western Blot assay using the biomarkers of the present disclosure in patients with Ta/T1 (non-muscle invasive) bladder carcinoma with healthy subjects and patients with T2/T3 (muscle invasive) bladder carcinoma with healthy subjects. This model assesses the biomarker efficiency to distinguish both non-muscle invasive (NMI; Ta/T1) and muscle invasive (MI; T2/T3) bladder carcinoma from healthy subjects based on data obtained from Western Blot data analysis of urine samples.
Figure 9:
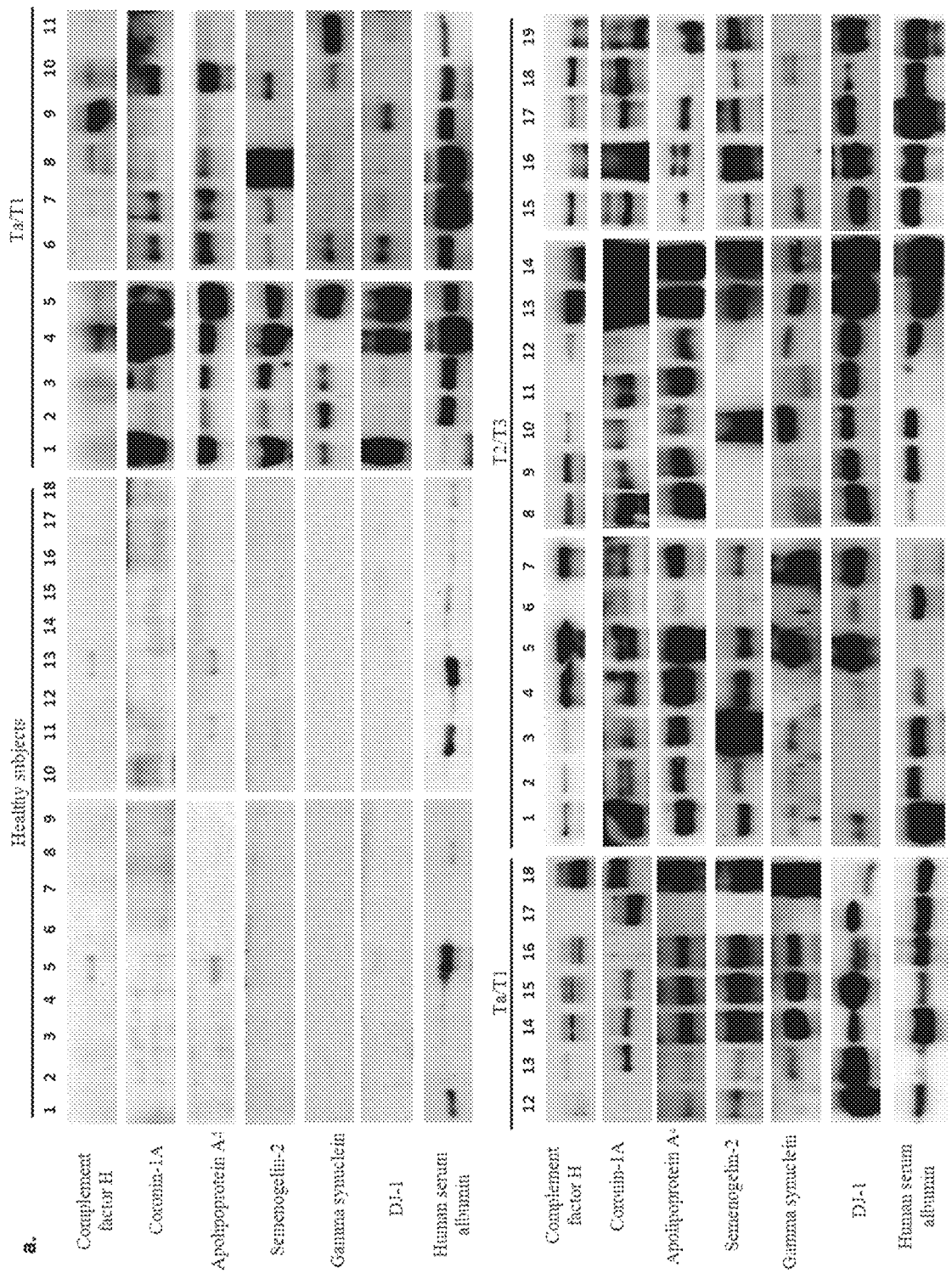
FIG. 9 shows Western Blot analysis comparing the expression of five biomarkers of the present disclosure (as well as control Complement factor H) in samples obtained from urine samples from 30 healthy subjects, 72 non-muscle invasive bladder carcinoma (Ta/T1) patients and 55 muscle invasive bladder carcinoma (T2/T3) patients. 100 μg protein from each voided urine sample of healthy subjects, non-muscle invasive (NMI; Ta/T1) and muscle invasive (MI; T2/T3) bladder carcinoma patient were western-blotted. The expression of the five biomarkers were compared to the Complement factor H. Human serum albumin protein was also Western-blotted for each sample to establish whether there is a correlation between each biomarker expression and hematuria.
Figure 10:
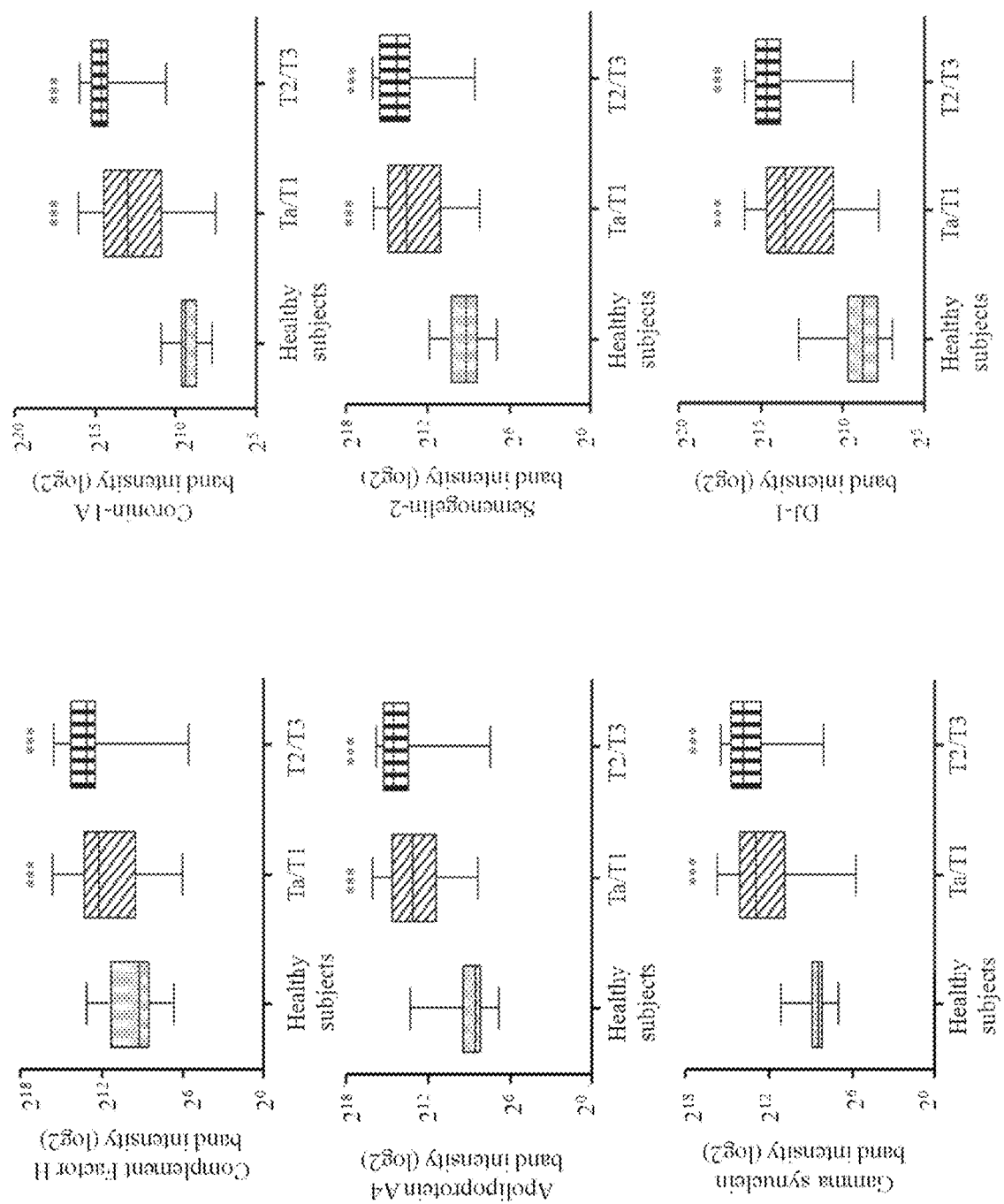
FIG. 10 shows a box and whiskers plot of log 2 band intensities of the results of Western Blot in FIG. 8, which were plotted for the five biomarkers and Complement factor H from all healthy subjects (n=30), Ta/T1 (n=72) and T2/T3 (n=55) bladder carcinoma urine samples. The box represents the lower quartile, median, and higher quartile; The whiskers show the minimum and maximum values. Mann-Whitney test was used to compute significance. p value for comparison to normal: ***$p<0.001$.

Western Blot Analysis of Healthy, Non-Invasive and Invasive BCa Stage Urine Samples Urine samples from 30 healthy subjects, 72 non-muscle invasive bladder carcinoma (Ta/T1) patients and 55 muscle invasive bladder carcinoma (T2/T3) patients were analysed. All non-muscle invasive bladder carcinoma and muscle invasive bladder carcinoma urine samples exhibited an elevated level of at least three out of the five biomarkers (FIG. 9). ROC curve, established using band intensity values, showed an AUC of 0.98 and 1.0 for healthy vs non-muscle invasive bladder carcinoma (Ta/T1) and healthy vs muscle invasive bladder carcinoma (T2/T3), respectively using the five biomarkers in combination (FIG. 7*b* and Table 9A and 9B).

TABLE 9A

Accuracy of the combination model in diagnosing Ta/T1 (non-muscle invasive) bladder cancer

| | Biomarkers | AUC | Sensitivity % | Specificity % | PPV % | NPV % | Overall accuracy % |
|---|---|---|---|---|---|---|---|
| ELISA | Complement factor H | 0.72 | 80 | 60 | 80 | 60 | 73.3 |
| | All five biomarkers in combination | 0.92 | 79.2 | 100 | 100 | 66.7 | 85.3 |
| Western blot | Complement factor H | 0.71 | 57.6 | 80 | 86.4 | 46.2 | 64.6 |
| | All five biomarkers in combination | 0.98 | 93.9 | 96.7 | 98.4 | 87.9 | 94.8 |
| | Three biomarkers (Coronin-1A, Apolipoprotein A4, DJ-1) in combination | 0.97 | 92.4 | 93.3 | 96.8 | 84.8 | 92.7 |
| | Four biomarkers (Coronin-1A, Apolipoprotein A4, Semanogelin-2, DJ-1) in combination | 0.98 | 90.9 | 96.7 | 98.4 | 82.9 | 92.7 |

Abbreviation: AUC, area under the curve; PPV, positive predictive value; NPV, negative predictive value.

TABLE 9B

Accuracy of the combination model in diagnosing T2/T3 (muscle invasive) bladder cancer

| | Biomarkers | AUC | Sensitivity % | Specificity % | PPV % | NPV % | Overall accuracy % |
|---|---|---|---|---|---|---|---|
| ELISA | Complement factor H | 0.51 | 77.8 | 40 | 70 | 50 | 64.3 |
| | All five biomarkers in combination | 0.94 | 86.4 | 100 | 100 | 76.9 | 90.6 |
| Western blot | Complement factor H | 0.88 | 92.9 | 76.7 | 78.8 | 92 | 84.5 |
| | All five biomarkers in combination | 1.0 | 100 | 100 | 100 | 100 | 100 |
| | Three biomarkers (Coronin-1A, Apolipoprotein A4, DJ-1) in combination | 1.0 | 100 | 100 | 100 | 100 | 100 |
| | Four biomarkers (Coronin-1A, Apolipoprotein A4, Semanogelin-2, DJ-1) in combination | 1.0 | 100 | 100 | 100 | 100 | 100 |

Abbreviation: AUC, area under the curve; PPV, positive predictive value; NPV, negative predictive value.

The data from Western Blot analyses (FIG. 9) showed perfect concordance with the RT-PCR data (FIG. 8), indicating that the five biomarkers were significantly enriched in urine samples of bladder cancer patients as compared with that of healthy subjects. Representative MS spectra of the five potential markers are also in good agreement with RT-PCR and Western Blot data (FIG. 11).

Urinary Biomarkers and Haematuria

Haematuria occurs in a number of patients with urinary tract disease and, thus, haematuria could affect a diagnosis of bladder carcinoma using the selected biomarkers of the present disclosure, as these proteins can also be found in blood; albeit, at low levels. Table 10 provides the prevalence of four of the biomarkers in plasma based on a database search.

TABLE 10

Biomarker concentration in blood plasma obtained from database

| Protein | Uniprot Name | Accession Number | Concentration by MS |
|---|---|---|---|
| Coronin-1A | COR1A_HUMAN | P31146 | 41 ng/ml |
| Apolipoprotein A4 | APOA4_HUMAN | P06727 | 30-50 µg/ml |
| Semenogelin-2 | SEMG1_HUMAN | P04279 | 6 ng/ml |
| Gamma synuclein | SYUG_HUMAN | O76070 | — |
| DJ-1 | PARK7_HUMAN | Q99497 | 23 ng/ml |
| Complement H | CFAH_HUMAN | P08603 | 30-120 µg/ml |

All data are taken from http://www.plasmaproteomedatabase.org/

The literature search also showed quite large variation in the concentration of the biomarkers. Thus, in the present study, Western Blot analysis was used to determine the expression of these five biomarkers in plasma and in white blood cells from four blood samples. All of the biomarkers were expressed in plasma but only Coronin-1A expression was visible in white blood cell extracts. To compute the correlation of these biomarkers with plasma, the Western Blot intensity of the biomarkers in blood and urine samples was quantified and normalized to human serum albumin (HSA) values in each respective sample. When analysed using Box and Whiskers plot, the data portrayed, all of the five biomarkers possess significantly higher relative expression level in Ta/T1 and T2/T3 urine samples compared to healthy subject urine sample or blood plasma (FIG. 6). Moreover, only Coronin-1 A shows marginal correlation with human serum albumin levels using Pearson Correlation test (Table 11). Thus, it is concluded that the urine biomarkers of the present disclosure were not expressed as a result of haematuria in the samples.

TABLE 11

Pearson correlation analysis of blood plasma and white blood cell with biomarkers: Pearson correlation coefficient (r) for the biomarkers in urine and blood plasma samples from healthy subjects, Ta/T1 bladder carcinoma (non-muscle invasive, NMI), and T2/T3 bladder carcinoma (muscle invasive, MI) patients.

| Biomarkers | Healthy Subjects Pearson r | Ta/T1 bladder carcinoma Samples (non-muscle invasive) Pearson r | T2/T3 bladder carcinoma Samples (muscle invasive) Pearson r |
|---|---|---|---|
| Coronin-1A | +0.1874 | +0.3198 | +0.4320 |
| Apolipoprotein A4 | +0.4570 | −0.1138 | +0.1753 |
| Semenogelin-2 | +0.3112 | +0.1645 | +0.2603 |
| Gamma synuclein | +0.3986 | −0.035 | −0.1208 |
| DJ-1 | +0.3198 | +0.0092 | +0.1300 |

Next, the present disclosure sought to correlate Coronin-1A expression with white blood cell count, making the assumption that human serum albumin originated only from blood rather than from defective kidney filtration. The present study found at least a 289-fold increase in the actual band intensity of Coronin-1A in urine as compared to what could have theoretically originated from white blood cells (see below). This analysis thus allows the exclusion of any significant contribution of white blood cells to Coronin-1A content.

Correlation Analysis of White Blood Cells (WBC) in Urinary Hematuria and Coronin-1A Biomarker Expression Concentration of albumin in blood (reported in literature)=40 µg/µl;

Concentration range of albumin in BCa patient urine samples (deduced from our experimental analysis)=0.012-2.56 µg/µl (Further calculations were done using the higher limit of the range);

Average albumin concentration in BCa patient urine samples=1.18 µg/µl;

Hence approx. volume of blood in urine=(1/40)*1.18=0.0295 µl [Assumption: Albumin source is solely blood];

No. of WBC/µl of blood (reported in literature)=approx. 5000;

Hence, 0.0295 µl of blood in urine contains=(5000*0.0295)=147.5 WBCs;

Weight of a single cell (reported in literature)=$3.5*10^{-3}$ µg;

Amount of protein/cell (reported in literature)=0.0007 µg [Protein weight is 20% of cells weight];

Approximately 40 µg of lysed WBC, obtained from buffy coat would be derived from=(1/0.0007)*40=57142.86 WBCs [Approx. 57,000 WBCs];

Coronin-1A blot intensity of 57,000 WBC lysate is =34403 [obtained from WB experiment conducted in the lab where the present study is conducted];

Hence, 147.5 WBCs if lysed in urine would produce an intensity of =(34,403/57000)*147.5=89.025 intensity;

Actual Coronin-1A intensity obtained from BCa urine sample blot=25,788.58 (averaged value);

Fold change in actual blot intensity compared to theoretically originated=(25,788.58/89.025)=289.68.

Hence, the present study confirmed that there is no correlation between serum albumin with Coronin-1A expression and now the difference in expression of this biomarker statistically calculated and experimentally obtained proves that the major contributor of Coronin-1A in BCa patient urine is not lysed white blood cell but the bladder tumor.

Figure 13:
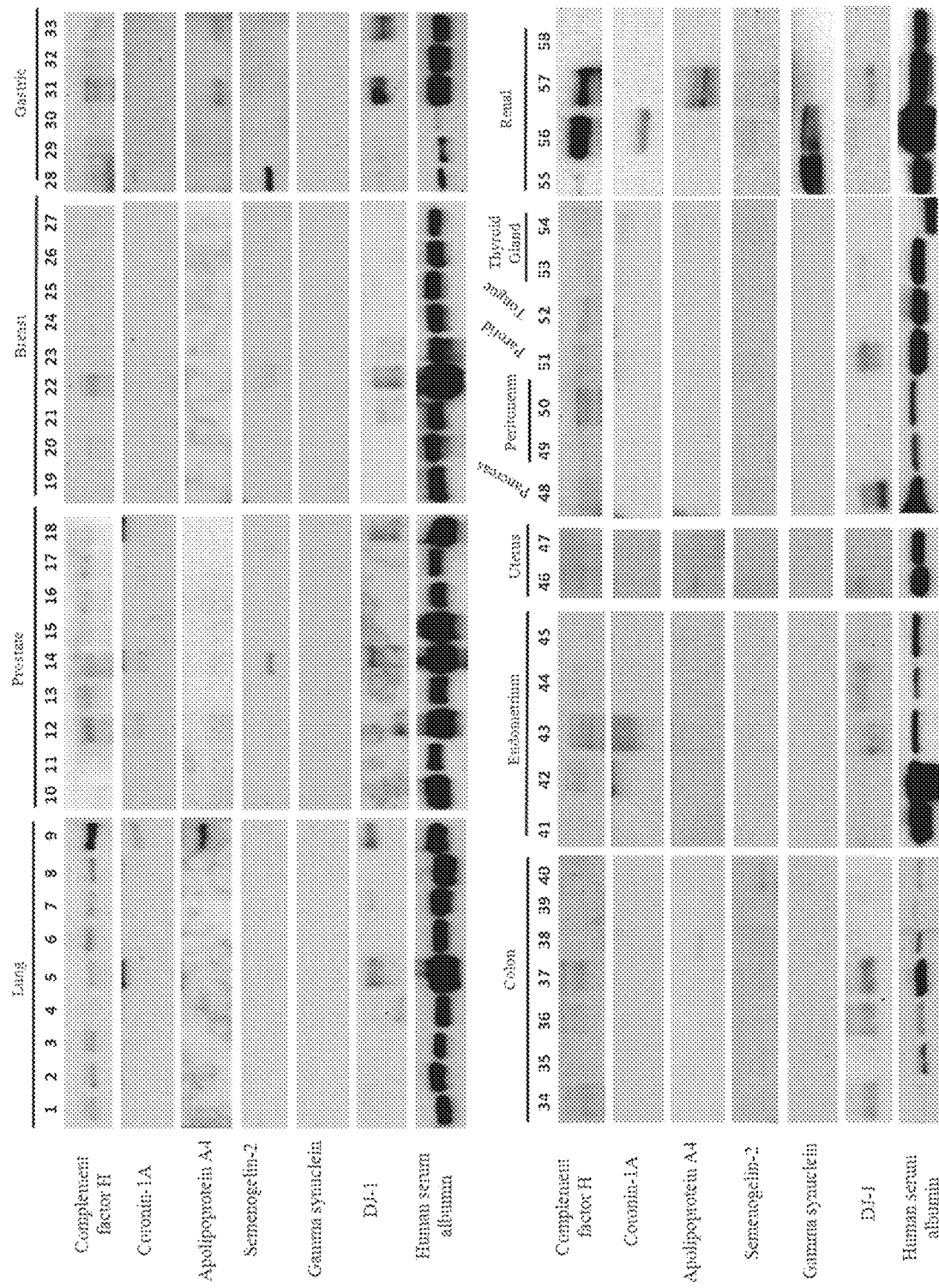
FIG. 13 shows Western Blot analysis comparing the expression of five biomarkers of the present disclosure (as well as control Complement factor H and human serum albumin, which was determined for each sample to establish whether there is a correlation between biomarker expression and haematuria) in urine samples obtained from non-bladder cancer patients who are suffering from other types of cancers.

Biomarker Prevalence in Urine Samples from Non-Bladder Cancer Patients and Patients Suffering from Various Chronic Diseases To further evaluate the specificity of the biomarkers of the present disclosure in bladder cancer, Western Blotting analysis was performed on 84 urine samples from non-bladder cancer patients and 120 urine samples from patients suffering from diverse chronic ailments (Table 6). The vast majority of samples were completely negative for these five biomarkers; albeit, in some instances, the sporadic expression of one biomarker was observed (FIG. 12a, FIG. 12b and FIG. 13).

Diagnostic Model to Analyse Combinations of the Five Biomarkers

The present study developed a diagnostic model using Lasso regression to evaluate the clinical utility of different combinations of all five urine biomarkers (Table 12A and 12B).

TABLE 12A

Accuracies and thresholds of biomarkers in Ta/T1 diagnosis using both ELISA and Western Blot urine sample data analysis.

| | Biomarkers | AUC | Threshold (ng/ml) or intensity | Sensitivity % | Specificity % | PPV % | NPV % | Overall Accuracy % |
|---|---|---|---|---|---|---|---|---|
| ELISA | Complement factor H | 0.72 | 392.4 | 80 | 60 | 80 | 60 | 73.3 |
| | Coronin-1A | 0.81 | 2.31 | 66.7 | 100 | 100 | 55.6 | 76.5 |
| | Apolipoprotein A4 | 0.93 | 0.5 | 79.2 | 100 | 100 | 66.7 | 85.3 |
| | Semenogelin-2 | 0.73 | 29.1 | 66.7 | 80 | 88.9 | 50 | 70.6 |
| | Gamma synuclein | 0.88 | 2.4 | 87.5 | 90 | 95.5 | 75 | 88.2 |
| | DJ-1 | 0.94 | 2.4 | 83.3 | 100 | 100 | 71.4 | 88.2 |

TABLE 12A-continued

Accuracies and thresholds of biomarkers in Ta/T1 diagnosis using both ELISA and Western Blot urine sample data analysis.

| | Biomarkers | AUC | Threshold (ng/ml) or intensity | Sensitivity % | Specificity % | PPV % | NPV % | Overall Accuracy % |
|---|---|---|---|---|---|---|---|---|
| Western blot | Complement factor H | 0.71 | 4158 | 57.6 | 80 | 86.4 | 46.2 | 64.6 |
| | Coronin-1A | 0.92 | 2029.5 | 75.8 | 100 | 100 | 65.2 | 83.3 |
| | Apolipoprotein A4 | 0.93 | 939.2 | 87.9 | 90 | 95.1 | 77.1 | 88.5 |
| | Semenogelin-2 | 0.91 | 879.7 | 92.4 | 76.7 | 89.7 | 82.1 | 87.5 |
| | Gamma synuclein | 0.89 | 1145.2 | 81.8 | 96.7 | 98.2 | 70.7 | 86.5 |
| | DJ-1 | 0.91 | 2864.8 | 74.2 | 96.7 | 98 | 63 | 81.3 |

Abbreviation: AUC, area under the curve; PPV, positive predictive value; NPV, negative predictive value.

TABLE 12B

Accuracies and thresholds of biomarkers in T2/T3 diagnosis using both ELISA and Western Blot urine samples data analysis.

| | Biomarkers | AUC | Threshold (ng/ml) or intensity | Sensitivity % | Specificity % | PPV % | NPV % | Overall Accuracy % |
|---|---|---|---|---|---|---|---|---|
| ELISA | Complement factor H | 0.51 | 233.1 | 77.8 | 40 | 70 | 50 | 64.3 |
| | Coronin-1A | 0.85 | 1.9 | 81.8 | 90 | 94.7 | 69.2 | 84.4 |
| | Apolipoprotein A4 | 1.0 | 0.5 | 90.9 | 100 | 100 | 83.3 | 93.8 |
| | Semenogelin-2 | 0.79 | 30.0 | 77.3 | 80 | 89.5 | 61.5 | 78.1 |
| | Gamma synuclein | 0.79 | 2.35 | 72.7 | 90 | 95.5 | 75 | 88.2 |
| | DJ-1 | 0.99 | 2.3 | 95.5 | 100 | 100 | 90.9 | 96.9 |
| Western blot | Complement factor H | 0.88 | 2299.9 | 92.9 | 76.7 | 78.8 | 92 | 84.5 |
| | Coronin-1A | 0.99 | 1584.5 | 100 | 96.7 | 96.6 | 100 | 98.3 |
| | Apolipoprotein A4 | 0.95 | 1681.9 | 92.9 | 93.3 | 92.9 | 93.3 | 93.1 |
| | Semenogelin-2 | 0.94 | 3947.6 | 89.3 | 100 | 100 | 90.9 | 94.8 |
| | Gamma synuclein | 0.96 | 818.9 | 92.9 | 96.7 | 96.3 | 93.5 | 94.8 |
| | DJ-1 | 0.99 | 2123.4 | 96.4 | 93.3 | 93.1 | 96.6 | 94.8 |

Abbreviation: AUC, area under the curve; PPV, positive predictive value; NPV, negative predictive value.

The diagnostic performances of each of the five biomarkers were computed separately and in various combinations using ELISA and Western Blotting data. Sensitivity and specificity, along with the cut-off values for each biomarker, are listed in Table 12 A and 12 B. In contrast with the results in Example 1, using expression data from ELISA, this updated study (Example 2) found that a diagnostic model that combined all five biomarkers was the most accurate, achieving an AUC of 0.92 and an overall accurate of 85.3% (sensitivity, 79.2%; specificity, 100%) Table 9A in differentiating Ta/T1 bladder cancer patients from healthy subjects. Similarly, for diagnosing T2/T3 bladder cancer patients in updated study (Example 2), the diagnostic model achieved an AUC of 0.94 and an overall accuracy of 90.6% (sensitivity, 86.4%; specificity, 100%; in Table 9 B. In comparison, Complement factor H showed an AUC of 0.72 and an overall accuracy of 73.3% (sensitivity, 80%; specificity, 60%) for a Ta/T1 bladder cancer diagnosis, and an AUC of 0.51 and an overall accuracy of 64.3% (sensitivity, 77.8%; specificity, 40%) for T2/T3 bladder cancer diagnosis (Table 9 A and 9 B).

Likewise, using the Western Blot data, this updated study (Example 2) found that a diagnostic model that combined all five biomarkers was the most accurate in achieving an AUC of 0.98 and an overall accuracy of 94.8% (sensitivity, 93.9%; specificity, 96.7%) for a Ta/T1 bladder cancer diagnosis. Thus, the diagnostic model combining all five biomarkers was highly sensitive and specific, outperforming the FDA-approved complement factor H by 27-30% and conventional cytology or any existing biomarkers reported to date for a Ta/T1 bladder cancer diagnosis.

Advanced MS-based isotope dimethyl labelling technology allowed the inventors of the present disclosure to identify a panel of novel biomarkers with high precision for bladder cancer diagnosis. In this study, urine samples were analysed using this state-of-art approach to relatively quantify the urine proteome of bladder carcinoma patients against that of healthy subjects. Five biomarkers were selected from MS data following extensive filtering and literature survey. The five putative biomarkers were subsequently validated by RT-PCR, Western Blot and ELISA assays. The urinary concentration of these five biomarkers was elevated in patients with bladder carcinoma as compared to that in healthy subjects.

Using data from ELISA and Western Blot, the diagnostic performance of these five putative biomarkers for bladder carcinoma detection was vigorously validated, and it was found that, in one example, it is necessary to combine all five biomarkers for an accurate diagnosis. None of the healthy subjects had detectable concentrations of these five biomarkers. In the present study, the five biomarkers of the present disclosure was also compared with current biomarkers, including the FDA-approved biomarker Complement factor H. Complement factor H exhibited 60% specificity for benign renal diseases and urinary tract infections as well as other cancer types, such as prostate cancer or renal cancer. Unlike Complement factor H, the urine biomarkers of the present disclosure were able to differentiate patients with bladder carcinoma from those with benign conditions, such as inflammatory bladder, benign prostatic hyperplasia or nephrolithiasis possibly associated with haematuria. The experimental study as described herein only infrequently detected some of the markers of the present disclosure in the urine of patients affected by chronic diseases or some cancer types that were tested in this study.

The FDA-approved biomarker NMP22 has been shown to be affected by haematuria in the urine. Hence, the present study also considered the possible contribution of these biomarkers by blood contamination. The human serum albumin level in urine varies considerably, and can also be detected in healthy subjects. Notably, urine from patients with chronic diseases, such as diabetes, has a much higher level of human serum albumin than that from many of bladder carcinoma patients observed in the present disclosure. Therefore, human serum albumin does not always reflect blood contamination. In addition, the contribution of these biomarkers from plasma or white blood cell contamination cannot account for the levels of these biomarkers detected following low-speed centrifugation of urine.

In Example 2, all five biomarkers showed equally enriched expression in immunohistochemically stained bladder carcinoma tissue (FIG. 14), and the statistical analysis demonstrated the significance of a diagnostic model using all five biomarkers for bladder carcinoma detection.

The invention claimed is:

1. A detection system comprising a) a receiving section to receive a sample from a patient suspected of having bladder cancer and b) a detection section comprising antibodies, for detecting at least three bladder cancer protein biomarkers, wherein the biomarkers are selected from the group consisting of Coronin-1A, Apolipoprotein A-IV, Semenogelin-2, Gamma-synuclein and DJ-1, and further wherein at least two of the biomarkers are Coronin-1A and Apolipoprotein A-IV.

2. The detection system of claim 1, wherein the detection section comprises antibodies for binding or specifically binding to the biomarkers.

3. The detection system of claim 1, wherein the system is a biochip or test strip or microtiter plate.

4. The detection system of claim 1, wherein the sample is a fluid sample.

5. The detection system of claim 4, wherein the fluid sample is urine or voided urine.

6. The detection system of claim 1, wherein the biomarker is indicative for early stage (Ta/T1) and/or late stage (T2/T3) bladder cancer.

7. The detection system of claim 1, wherein the biomarkers are Coronin-1A, Apolipoprotein A-IV, Semenogelin-2, Gamma-synuclein and DJ-1.

8. The detection system of claim 1, wherein detection is to be carried out using a molecular biological method selected from the group consisting of Western Blot, dot blot, and an immunological method, wherein the immunological method is ELISA.

9. A kit comprising a detection system according to claim 1.

* * * * *

```
                            SEQUENCE LISTING

<160> NUMBER OF SEQ ID NOS: 14

<210> SEQ ID NO 1
        <211> LENGTH: 20
        <212> TYPE: DNA
        <213> ORGANISM: Artificial Sequence
        <220> FEATURE:
        <223> OTHER INFORMATION: Synthetic Polynucleotide

<400> SEQUENCE: 1
cacacaagat ggatggtcgc                                              20

<210> SEQ ID NO 2
        <211> LENGTH: 20
        <212> TYPE: DNA
        <213> ORGANISM: Artificial Sequence
        <220> FEATURE:
        <223> OTHER INFORMATION: Synthetic Polynucleotide

<400> SEQUENCE: 2
ggatggcagg caacgtctat                                              20

<210> SEQ ID NO 3
        <211> LENGTH: 19
        <212> TYPE: DNA
        <213> ORGANISM: Artificial Sequence
        <220> FEATURE:
        <223> OTHER INFORMATION: Synthetic Polynucleotide

<400> SEQUENCE: 3
cttcagccgc atgagtgag                                               19

<210> SEQ ID NO 4
        <211> LENGTH: 21
        <212> TYPE: DNA
        <213> ORGANISM: Artificial Sequence
        <220> FEATURE:
        <223> OTHER INFORMATION: Synthetic Polynucleotide

<400> SEQUENCE: 4
aggtagacga tgttggtgtc a                                            21

<210> SEQ ID NO 5
        <211> LENGTH: 19
        <212> TYPE: DNA
        <213> ORGANISM: Artificial Sequence
```

```
<220> FEATURE:
<223> OTHER INFORMATION: Synthetic Polynucleotide

<400> SEQUENCE: 5
cccagcaact caatgccct                                              19

<210> SEQ ID NO 6
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 6
ccttcagttt ctccgagtcc t                                           21

<210> SEQ ID NO 7
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 7
ccaacatgga cccaaagaca t                                           21

<210> SEQ ID NO 8
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 8
tgtacgtgaa gacgggtatg a                                           21

<210> SEQ ID NO 9
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 9
caagaagggc ttctccatcg ccaagg                                      26

<210> SEQ ID NO 10
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 10
cctctttctc tttggatgcc acaccc                                      26

<210> SEQ ID NO 11
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 11
tgcgttcact ttcagcct                                               18
```

```
<210> SEQ ID NO 12
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 12
tgtgacttcc atacttccgc                                               20

<210> SEQ ID NO 13
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 13

Lys Glu Lys Glu Ser Gln Asp Lys Thr Leu Ser Leu Pro
1               5                   10

<210> SEQ ID NO 14
<211> LENGTH: 50
<212> TYPE: PRT
<213> ORGANISM: Artificial Sequence
<220> FEATURE:
<223> OTHER INFORMATION: Synthetic Polypeptide

<400> SEQUENCE: 14

Gly Gln Lys Gly Gln His Tyr Phe Gly Gln Lys Asp Gln His Thr
1               5                   10                  15

Lys Ser Lys Gly Ser Phe Ser Ile Gln His Thr Tyr His Val Asp Ile
                20                  25                  30

Asn Asp His Asp Trp Thr Arg Lys Ser Gln Gln Tyr Asp Leu Asn Ala
        35                  40                  45

Leu His
    50
```